(12) United States Patent
Shibata et al.

(10) Patent No.: US 7,599,545 B2
(45) Date of Patent: Oct. 6, 2009

(54) METHOD AND ITS APPARATUS FOR INSPECTING DEFECTS

(75) Inventors: Yukihiro Shibata, Fujisawa (JP); Shunji Maeda, Yokohama (JP); Hitoshi Kubota, Fujisawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1023 days.

(21) Appl. No.: 10/893,988

(22) Filed: Jul. 20, 2004

(65) Prior Publication Data
US 2005/0052642 A1     Mar. 10, 2005

(30) Foreign Application Priority Data
Sep. 5, 2003     (JP) .............................. 2003-313897

(51) Int. Cl.
*G06K 9/00*     (2006.01)
*H04N 7/18*     (2006.01)

(52) U.S. Cl. ........................... 382/141; 348/61; 348/81; 348/92; 348/125

(58) Field of Classification Search ......... 382/141–154; 348/61, 81, 92, 125–132
See application file for complete search history.

(56) References Cited

U.S. PATENT DOCUMENTS

| | | | | |
|---|---|---|---|---|
| 4,509,852 A * | 4/1985 | Tabarelli et al. | ................ | 355/30 |
| 5,444,529 A * | 8/1995 | Tateiwa | ....................... | 356/337 |
| 5,610,683 A * | 3/1997 | Takahashi | ..................... | 355/53 |
| 5,900,354 A * | 5/1999 | Batchelder | .................. | 430/395 |
| 6,630,996 B2 * | 10/2003 | Rao et al. | ................. | 356/237.5 |
| 6,788,477 B2 * | 9/2004 | Lin | ............................. | 359/820 |
| 6,867,844 B2 * | 3/2005 | Vogel et al. | .................... | 355/30 |
| 7,130,037 B1 * | 10/2006 | Lange | ...................... | 356/237.2 |
| 7,372,561 B2 * | 5/2008 | Shibata et al. | ............ | 356/237.5 |
| 2004/0125351 A1 * | 7/2004 | Krautschik | ................... | 355/53 |

FOREIGN PATENT DOCUMENTS

| | | |
|---|---|---|
| JP | 06-124873 | 5/1994 |
| JP | 10-154659 | 6/1998 |
| JP | 11-063944 | 3/1999 |
| JP | 11118728 | * 4/1999 |
| JP | 2000-155099 | 6/2000 |
| JP | 2001-356278 | 12/2001 |
| JP | 2002-350719 | 12/2002 |
| WO | WO 99/49504 | 9/1999 |

* cited by examiner

*Primary Examiner*—Daniel G Mariam
*Assistant Examiner*—Manav Seth
(74) *Attorney, Agent, or Firm*—Antonelli, Terry, Stout & Kraus, LLP.

(57) ABSTRACT

The present invention relates to a high-sensitivity inspection method and apparatus adapted for the fine-structuring of patterns, wherein defect inspection sensitivity is improved using the following technologies: detection optical system is improved in resolution by filling the clearance between an objective lens 30 and a sample 1, with a liquid, and increasing effective NA (Numerical Aperture); and when a transparent interlayer-insulating film is formed on the surface of the sample, amplitude splitting at the interface between the liquid and the insulating film is suppressed for reduction in the unevenness of optical images in brightness due to interference of thin-film, by immersing the clearance between the objective lens and the sample, with a liquid of a refractive index close to that of the transparent film.

30 Claims, 14 Drawing Sheets

FIG. 26

| Wafer location | Inspection sequence | | Method |
|---|---|---|---|
| Cassette | Waiting for the start of inspection | | |
| Transfer system | Wafer loading — S262 | | |
| Preparation chamber | V-notch matching (Theta prealignment of wafer) — S263 | | |
| | Pre-inspection liquid immersion — S264 | | |
| | Wafer interfacial bubble removal — S265 | | Wafer in-liquid spinning |
| | Removal of pre-inspection liquid (No liquid removal from water surface) — S266 | | Wafer in-liquid ultrasound vibration |
| | Wafer loading — S267 | | Depressurizing process |
| Inspection station | S268 — Supply liquid | Temperature adjustment | Thermoelectric cooling |
| | | Bubble removal | Depressurization |
| | | Oxygen concentration control | Atmosphere with low oxygen concentration |
| | S269 — Inspection liquid immersion | | Wafer total liquid immersion |
| | S270 — Wafer scanning and image detection (Image comparison: By image processor) | | Wafer local liquid immersion |
| | S271 — Removal of inspection liquid | | |
| Preparation chamber | Wafer unloading — S272 | S273 — Surface activation of liquid-immersed objective lens area during inspection waiting state | UV irradiation onto the wafer-facing side of objective lens during inspection waiting state |
| | S274 — Wafer drying | | Reduced-pressure IPA vaporizing |
| Transfer system | Wafer unloading — S275 | | Wafer spinning |
| Cassette | End of inspection | | Jet spraying of gas |

FIG.27A FIG.27B FIG.27C
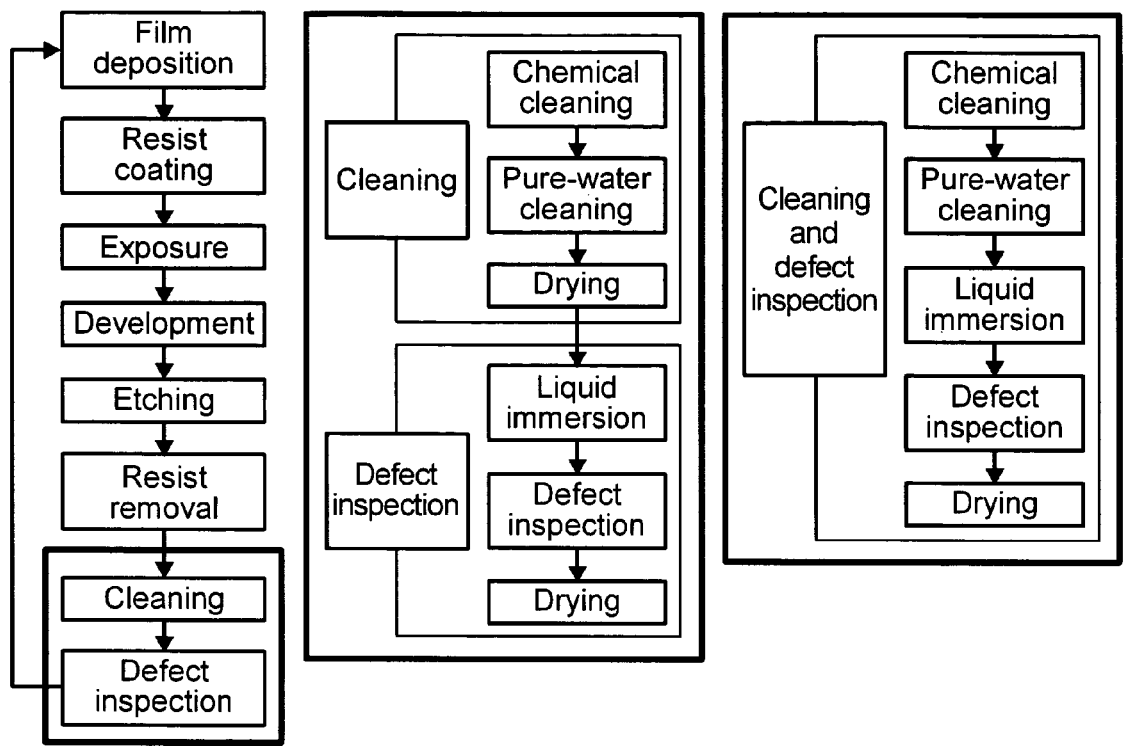
FIG.28
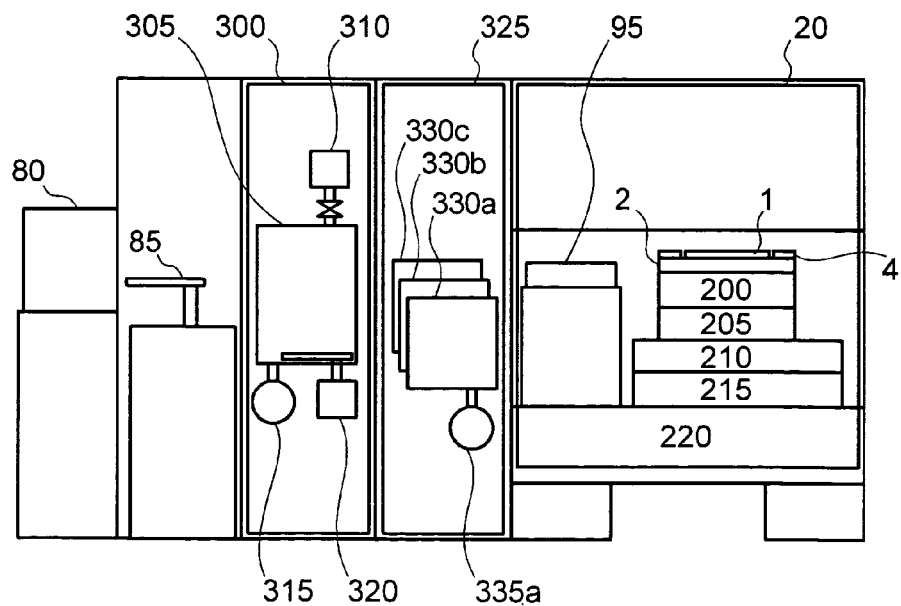

METHOD AND ITS APPARATUS FOR INSPECTING DEFECTS

BACKGROUND OF THE INVENTION

The present invention relates to a defect inspection method and defect inspection apparatus used to inspect and observe defects, foreign particle, and the like, on the micro-patterns formed on a substrate through a thin-film forming process represented by manufacturing processes for semiconductors or flat-panel displays.

Fine structuring of the patterns formed with photolithography is progressing with the enhancement of semiconductor integration density and the improvement of flat-panel display resolution. During the manufacturing processes for these products, after the patterns have been formed, they are subjected to defect inspection and/or the like in order to improve production yields. During the defect inspection, the patterns are detected as images by optical system etc., then these images are compared with those of adjacent dies (or cells), and defects are extracted on the basis of comparison results.

Incidentally, the resolution-improving technology disclosed in Japanese Patent Application Laid-Open Publication No. 2000-155099 (corresponding to U.S. application Ser. No. 09/397,334) is known as an ultrahigh-resolution detection technology that uses wavelength reduction and light polarization with conventional defect inspection optical system.

In the above ultrahigh-resolution detection technology that uses light polarization, specific polarized light is irradiated onto a sample via a dry-system objective lens by incident illumination, the light thus reflected/diffracted is captured by the same objective lens, and an image of the sample is detected using an image sensor. The conventional technology has had the characteristic that an optical image of the sample can be obtained with high contrast by detecting this image using only specific polarized components of the reflected/diffracted light.

In the generation of hyperfine-structuring into pattern sizes of sub-100 nm, however, pattern images have been becoming difficult to accurately detect, since sufficient resolution has not been made obtainable using only the resolution-improved defect inspection optical system mentioned above. The need is therefore arising to improve resolution by using defect inspection optical system enhanced further in numerical aperture (NA).

Additionally, in a sample, represented by a semiconductor wafer, that has undergone a thin-film forming process as the object to be inspected, a transparent film made of silicon dioxide ($SiO_2$), for example, is formed as an interlayer-insulating film. This insulating film has thickness unevenness in the wafer. During the inspection, such film thickness unevenness should originally not be detected since it has no fatal influence with respect to device characteristics. During observation through a dry-system lens, however, thin-film interference on the transparent film causes the unevenness of the film thickness to appear as the unevenness of brightness on the image detected. For example, during comparative inspection with respect to adjacent dies, if the transparent films on these adjacent dies are uneven in film thickness, differences in the brightness of the respective images detected will occur and an image of the object will be incorrect-detected as a defect image. Increasing an inspection threshold value in an attempt to avoid such incorrect-detection will pose the problem that total inspection sensitivity decreases.

In addition, since their pattern materials and surface irregularities will differ according to the manufacturing processes and product types, the objects to be subjected to defect inspection will be of various types and forms.

SUMMARY OF THE INVENTION

In one aspect, the present invention is a defect inspection method and defect inspection apparatus solving the above subjects, increasing effective NA for improved resolution, and thus allowing optical inspection and observation of defects down to substantially a sub-100 nm level or below.

In another aspect, the present invention is a defect inspection method and defect inspection apparatus allowing high-sensitivity inspection by minimizing any effects of the unevenness of transparent films in film thickness when comparative inspections with adjacent dies or the like are to be conducted.

An object of the present invention is to improve the resolution of a detection optical system by filling the clearance between its objective lens and the above-mentioned sample, with a liquid, and increasing effective NA (numerical aperture).

Another object of the present invention is to reduce the unevenness of brightness due to thin-film interference, by immersing, in a liquid of a refractive index close to that of a transparent film, the clearance between the objective lens and the sample so that even when a transparent interlayer-insulating film is formed on the surface of the sample, amplitude splitting at the interface between the liquid and the insulating film is suppressed.

Additionally, the present invention makes it possible, by detecting focus using the TTL (Through The Lens) scheme in which light is passed through the above-mentioned objective lens, to obtain highly accurate focus detection results substantially free from a focus detection error due to the unevenness of the liquid surface in terms of shape.

Furthermore, the present invention can take a compact apparatus construction in which only the clearance between the objective lens and the wafer is subjected to local liquid immersion.

In a yet another aspect, the present invention is a defect inspection method and defect inspection apparatus including a defect inspection process, wherein the defect inspection process further includes: an optical-image forming step for forming an optical image of a sample in detection optical system while the clearance between the sample and the detection optical system is being immersed in a liquid; a signal acquisition step for acquiring as an image signal by means of an image sensor the optical image of the sample that has been formed in the optical-image forming step; and a defect detection step for detecting defects on the sample by using the image signal acquired in the signal acquisition step.

In a further aspect, the present invention is characterized in that it includes, in the optical-image forming step of the above defect inspection process, a liquid supplying and discharging step for continuously supplying a liquid to the clearance between the sample and the detection optical system and continuously discharging an undersupply of the liquid.

The present invention is also characterized in that the liquid immersion mentioned above is the local liquid immersion conducted on the sample in the optical-image forming step of the above defect inspection process.

In addition, the present invention is characterized in that it realizes the above local liquid immersion by supplying the liquid in the direction where the sample is to be moved. The present invention is further characterized in that it realizes the local liquid immersion by supplying the liquid to a supply position before the view field of the detection optical system passes on the sample and discharging the liquid from a discharge position after the view field of the detection optical system passed on the sample.

Besides, the present invention is characterized in that the liquid immersion mentioned above is the sample total liquid immersion conducted in the optical-image forming step of the above defect inspection process.

Furthermore, the present invention is characterized in that in the optical-image forming step of the above defect inspection process, the sample is illuminated using either incident illumination, off-axis illumination, or a combination of both.

Besides, the present invention is characterized in that it includes, in the optical-image forming step of the above defect inspection process, a focus detection step for illuminating the sample via the detection optical system and obtaining, by use of the light reflected from the sample, focus detection information that represents the relationship between the focus of the detection optical system and the position of the sample.

In a further aspect, the present invention is a defect inspection method including a defect inspection process, the defect inspection process further including: an optical-image forming step for, while the clearance between a sample and the front-end portion of detection optical system is being immersed in a liquid, forming an optical image of the sample by detecting in a polarized fashion via the detection optical system the reflected/diffracted light obtained by elliptically polarized illumination of the sample; a signal acquisition step for acquiring as an image signal by an image sensor the optical image of the sample that has-been formed in the optical-image forming step; and a defect detection step for detecting defects on the sample by using the image signal acquired in the signal acquisition step.

Furthermore, the present invention is characterized in that it includes an inspection preparation step for immersing the sample in a liquid and conducting interfacial bubble removal of the sample prior to the defect inspection process.

Furthermore, the present invention is characterized in that it includes a post-process for drying the sample after the defect inspection process.

Furthermore, the present invention is characterized in that it includes the step of conducting a surface activation treatment on the liquid-immersed area of the detection optical system in the defect inspection process.

According to the present invention, immersing in a liquid the clearance between the objective lens and the sample makes it possible to improve resolution in proportion to a refractive index "n" of the liquid, and to suppress the unevenness in the brightness of images of adjacent dies or adjacent cells due to thin-film interference. Hence, inspection threshold values can be reduced and both the above-mentioned improvement and suppression are effective for the improvement of inspection sensitivity.

These and other objects, features, and advantages of the invention will be apparent from the following more particular description of preferred embodiments of the invention, as illustrated in the accompanying drawings.

BRIEF DESCRIPTION OF THE DRAWINGS

FIG. 26 is an explanatory diagram of a liquid-immersion inspection sequence according to the present invention.

FIGS. 27A, 27B, and 27C are diagrams each explaining a semiconductor-manufacturing process that employs liquid-immersion inspection according to the present invention.

FIG. 28 is a diagram showing an embodiment of an apparatus that has a liquid-immersion inspection function and a wafer-cleaning function according to the present invention.

DETAILED DESCRIPTION OF THE PREFERRED EMBODIMENTS

Embodiments of the present invention are described below using the accompanying drawings.

First, embodiments of the inspection that uses total liquid immersion are described using FIGS. 1 to 10, 26, 31, and 32.

Figure 1:
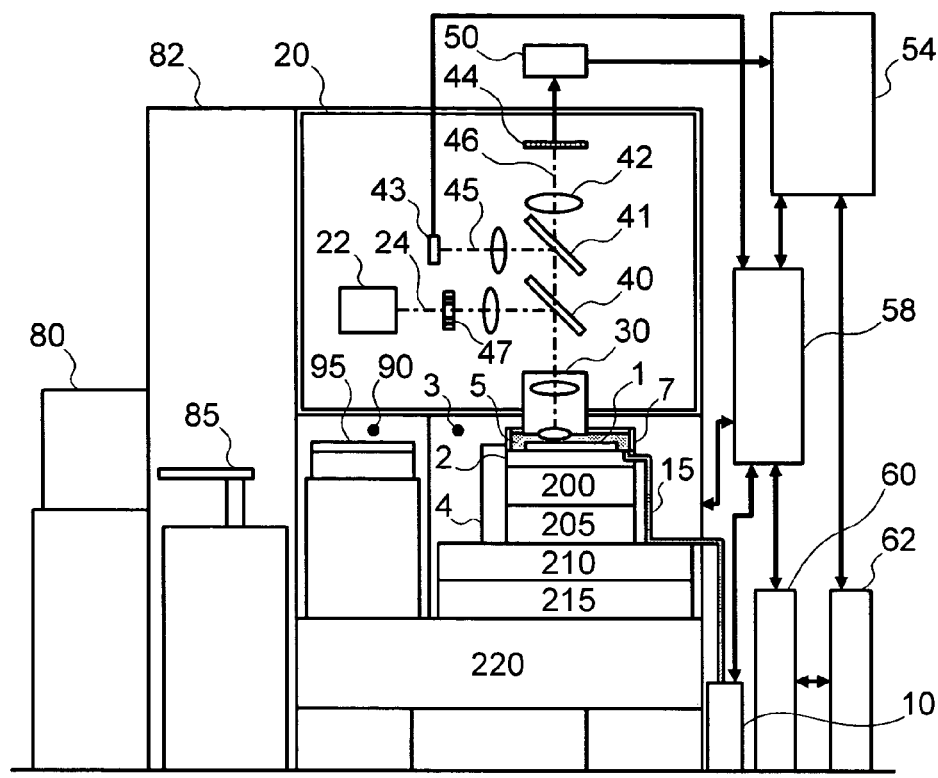
FIG. 1 is a configuration diagram showing an embodiment of an optical-type visual inspection apparatus that uses total liquid immersion according to the present invention.

An embodiment in which the present invention is applied to an optical-type visual inspection apparatus for semiconductor wafers is shown in FIG. 1. An inspection sequence and related methods are shown in FIG. 26. Referring back to FIG. 1, symbol 82 denotes an outer frame including a wafer transfer robot 85 in an optical-type visual inspection apparatus. Wafers to be inspected are stored in a cassette 80, and each of the wafers is transferred to an inspection preparation chamber 90 by a transfer system such as the wafer transfer robot 85 (step S262, FIG. 26), and then mounted on a wafer notch (or orientation flat) detector 90. On the notch detector 90, the wafer is pre-aligned in a required a direction (step S263). After this, the wafer undergoes pre-inspection liquid immersion (step S264), wafer interfacial bubble removal (step S265), and pre-inspection liquid removal (step S266: the liquid on the wafer surface, however, is not removed in this step). Wafer interfacial bubble removal is likely to be accomplished by methods of wafer in-liquid spinning, wafer in-liquid ultrasound vibration, or a depressurizing process. The wafer that has thus been treated is transferred to an inspection station 3 (step S267). In the inspection station 3, the wafer 1 is subjected to total liquid immersion (step S269) in which step the wafer is immersed in a liquid 5 with which a liquid tank 7 is filled. Temperature adjustment using a thermoelectric cooling method (or the like) for suppressing changes in a refractive index of the liquid, bubble removal that uses a pressure reduction method for removing the micro-bubbles contained in the liquid, and oxygen concentration control using an oxygen concentration adjustment method for preventing wafer oxidation are conducted on the above-mentioned liquid (step 268). The liquid tank 7 is connected to a liquid supplying and discharging unit 10 via a pipe 15. After loading of the wafer 1, the liquid 5 is supplied (step S269), and before unloading, the liquid 5 is discharged (step S271). A chuck 2 and the liquid tank 7 are mounted on a Z-direction stage 200, a θ-direction stage 205, an X-direction stage 210, and a Y-direction stage 215. These stages and an optical system 20 forming an image of the wafer 1 are further mounted on a stone surface plate 220.

Next, wafer scanning and image detection are conducted to inspect defects (step S270). Namely, illumination light 24 which be emitted from a light source 22 of the optical system 20 is reflected by a beam splitter 40. The reflected illumination light is irradiated onto the wafer 1 via an objective lens 30 and the liquid 5 by incident illumination. The light that has reflected and diffracted from the surface of the wafer 1 reaches the beam splitter 40 via the liquid 5 and the objective lens 30 once again. The light, after passing through the beam splitter 40, enters a beam splitter 41 that branches a focus detection optical path 45 and an image detection optical path 46. Light that has passed through the beam splitter 41 reaches an image sensor 44 to form an image of the wafer 1 thereon. Light that has been reflected by the beam splitter 41 is light used to detect an out-of-focus level between the wafer 1 and the objective lens 30, and the light enters a focus detection sensor 43. Focus is detected by, for example, projecting onto the wafer 1 a striped pattern 47 disposed on an illumination optical path, and then detecting with the focus detection sensor 43 an image of the striped pattern reflected by the wafer 1. It is desirable that this image of the striped pattern 47 should have already been separated from the view field detected by the image sensor 44. Contrast of the image thus detected is calculated at a mechanical controller 58 and if defocusing is occurring, the Z-stage 200 is driven for focusing. An optical image formed on the image sensor 44 is thus focused. In the focus detection scheme that uses liquid immersion, high focus-detection accuracy substantially insusceptible to the unevenness of the liquid 5 in surface shape (for example, the unevenness of the liquid 5 in surface shape, caused by the occurrence of waves on the surface) or to a change in focal position with temperature of the liquid 5 can be obtained by detecting focus with the TTL scheme in which light is passed through the objective lens 30. Desirably, the light used for focus detection is either light whose wavelength region is equivalent to that of the image formed on the image sensor 44, or light whose chromatic aberration has been corrected for by the objective lens 30.

The image, after being detected by the image sensor 44, is converted into a digital image by an A/D converter 50 and then transferred to an image processor 54. In the image processor 54, images of adjacent dies (or cells) are compared to extract defects. If the image sensor 44 is of a linear image sensor type such as a TDI (Time Delay Integration) type, images are detected while the wafer 1 is being scanned at a fixed speed. The above-mentioned stages, the wafer transfer robot 85, the liquid supplying and discharging unit 10, and the like are controlled by the mechanical controller 58. The mechanical controller 58 controls the mechanical system in accordance with commands from an operating controller 60 which controls the entire apparatus. After the image processor unit 54 has detected defects, information on the defects is stored into a data server 62. The defect information stored includes defect coordinates, defect sizes, defect classification information, and the like. The defect information can be displayed/searched for using the operating controller 60.

Next, when defect inspection is completed, the immersion liquid for the inspection is removed from a liquid tank 7 (step S271) and then the wafer is unloaded (step S272). Following this, during a waiting state for next inspection, surface activation (treatment for retaining a hydrophilic property by a photocatalytic effect) is conducted on the liquid-immersed area of the objective lens 30 by, for example, irradiating ultraviolet (UV) light onto an opposite side of the objective lens 30 with respect to the wafer (step S273). It is to be assumed that the liquid-immersed area of the objective lens 30 is already provided with hydrophilic treatment.

Further, in the inspection preparation chamber 90 or the like, the unloaded wafer 1 is dried with reduced-pressure IPA (isopropyl alcohol) vaporizing, wafer spinning, gas jet spraying, or the like, in step S274. After being dried, the wafer 1 is carried out from a gate 137 by a transfer system such as the wafer transfer robot 85 (step S275). The gate 137 is opened and closed by an opening/closing unit 136 of the inspection preparation chamber 90 (or the like), shown in FIG. 9. Finally, the wafer 1 is returned to the cassette 80. All the inspection sequence is thus completed.

Next, two effects brought about by liquid-immersion inspection, irrespective of whether it uses total liquid immersion or local liquid immersion, namely, (1) a resolution improvement effect and (2) a thin-film interference suppression effect, are described below.

(1) Resolution Improvement Effect

Equation (1) is known as a general equation for calculating resolution R of optical system.

$$R=\lambda/(2NA) \quad (1)$$

where $\lambda$ denotes illumination wavelength and NA denotes a numerical aperture of the objective lens.

Also, NA refers to the refractive index "n" between the objective lens and the wafer, determined by equation (2).

$$NA=n\cdot\sin\theta \quad (2)$$

where $\theta$ denotes an angle range in which the objective lens 1 can capture only rays of all those diffracted/scattered at one point on the wafer.

For an ordinary dry-system objective lens, only air is present between the objective lens and a wafer to be inspected, and a refractive index is therefore 1. Effective NA, however, can be increased by filling the region between the objective lens and the wafer, with a liquid having a refractive index greater than 1.

For example, if the region between the objective lens 30 and the wafer 1 is filled with pure water, since a refractive index of the water is about 1.35 (at a wavelength of 365 nm), NA becomes about 1.35 times that of the dry-system objective lens. Resolution also correspondingly improves by about 1.35 times. An upper limit of NA that can be increased by the liquid-immersion objective lens 30 has a relationship with a total reflection angle of an interface at which the objective lens 30 and the liquid 5 come into contact. If the objective lens 30 uses quartz as a glass material for its front end, refractive index "n1" at a wavelength of 365 nm is about 1.48 times. If pure water is used as the liquid 5, refractive index "n" is about 1.35 times (when wavelength is 365 nm). The present embodiment assumes that the surface of the quartz at the front end of the objective lens 30 is parallel to the surface of the wafer 1 facing the lens. When light is irradiated from the light source 22 onto the objective lens 30, an incident angle of the light totally reflected by the quartz at the front end is defined as a critical angle "$\theta c$" determined by refractive index "n1" of the quartz and refractive index "n" of the liquid 5 (here, pure water), as shown in equation (3).

$$\theta c \geq \sin^{-1}(n1/n) \quad (3)$$

The critical angle $\theta c$ is equivalent to an incident angle of 66°. At this critical angle, no light is allowed to pass through to the liquid 5. For practical purposes, 90% or more of the light passed from the quarts at the front end of the objective lens 30 to the liquid 5 is required (for random polarizing) and the incident angle (angle of incidence from the quartz side to the liquid side) in that case becomes about 56°. This angle of 56° is equivalent to an incident angle of 65° on the wafer 1. Accordingly, an absolute value of NA at the liquid 5 is equivalent to 0.91 (NA in the liquid 5). When converted into an equivalent of a dry-system objective lens, the absolute NA value of 0.91 becomes equal to 1.23. For practical use, therefore, the absolute NA value of 1.23, obtained by the above conversion, is the upper-limit value (when the wavelength is 365 nm). However, this is such an extent that even when the wavelength differs, the absolute NA value slightly changes in upper limit. In this way, the present invention allows the absolute value of NA to range from about 0.80 to about 1.23, by using liquid immersion.

By virtue of the above-described NA enhancement effect obtained using the liquid-immersion objective lens 30, microdefects unable to be imaged with a dry-system objective lens can be detected as high-contrast images with the liquid-immersion objective lens. Hence, defect detection sensitivity can be improved.

(2) Thin-Film Interference Suppression Effect

Figure 2A:
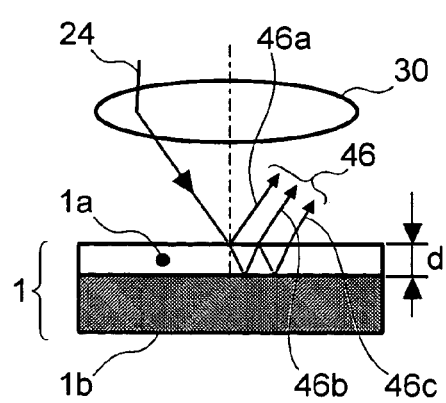
FIGS. 2A and 2B are explanatory diagrams of the thin-film interference suppression effect obtained from liquid immersion according to the present invention.
Figure 2B:
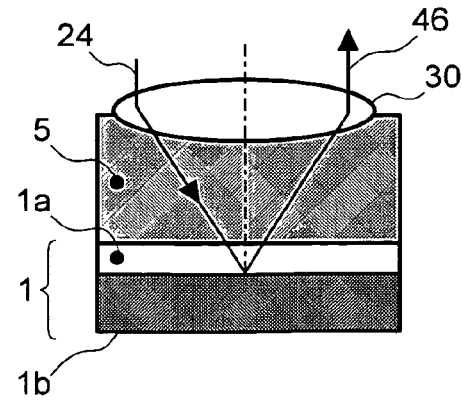

The thin-film interference suppression effect is shown using FIGS. 2A and 2B. An example of thin-film interference suppression using a dry-system objective lens is shown in FIG. 2A. A wafer 1 is illuminated via an objective lens 30. The wafer 1 has a deposited insulating film 1a (formed of $SiO_2$, for example) on its ground layer silicon 1b. The insulating film 1b is optically transparent, and illumination light 24 is amplitude-split into light 46a reflected by a top layer of the insulating film 1a, and light passing through the insulating film 1a. Light that has passed through the insulating film 1a is further split into light 46b reflecting from the ground layer 1b and passing through an interface between air and the insulating film, and light reflecting from the interface. Light that has reflected from the interface between air and the insulating film 1a repeats multiple reflecting to generate light 46c that exits into the air. An optical image formed by the objective lens is determined by interference intensity of the light 46a, 46b, 46c. The interference is referred to as thin-film interference. Since intensity of the thin-film interference is a function of a film thickness "d" of the insulating film 1a, if the film thickness "d" becomes unevenness, the optical image also becomes unevenness in brightness. The unevenness of the film thickness has no fatal influence with respect to device characteristics, and should originally not be detected as a defect. For defect inspection based on die comparisons, however, if the unevenness of the insulating film 1a in film thickness exists between adjacent dies, since the brightness between the images will also be differ, the unevenness of the film thickness is more likely to be incorrect-detected as a defect. Although a defect inspection threshold value needs to be increased to prevent such incorrect-detection, increasing the threshold value poses the problem that inspection sensitivity decreases.

For this reason, a technique for suppressing thin-film interference for improved inspection sensitivity has been desired. This technique is shown in FIG. 2B. Similarly to item (1) above, a clearance present between an objective lens 30 and a wafer 1 is immersed in a liquid having a refractive index close to that of an insulating film 1a. In this example, although illumination light 24 illuminates the insulating film 1a via a liquid 5, if the liquid 5 and the insulating film 1a have the same refractive index, amplitude splitting at an interface between the liquid 5 and the insulating film 1a does not occur and all light enters the insulating film 1a. Light that has passed through the insulating film 1a reflects from a ground layer 1b and is captured by the objective lens 30. Accordingly, amplitude splitting does not occur at a top layer of the insulating film 1a, and thin-film interference does not occur, either. Hence, it becomes possible to suppress unevenness of an image in brightness due to that of the insulating film 1a in film thickness, and thus to suppress defect incorrect-detection due to the unevenness of the film thickness. Consequently, high-sensitivity inspection can be implemented since an inspection threshold can be set to have a trifle small value.

If the insulating film 1a is formed of $SiO_2$, a refractive index thereof is 1.48 at a wavelength of 365 nm. Therefore, the liquid 5 for suppressing thin-film interference due to the insulating film 1a is preferably a liquid (pure water, alcohol-containing liquid, or mixture of both) that has a refractive index equivalent to that of the insulating film 1a. However, even when pure water having a refractive index of 1.35 at a wavelength of 365 nm is used as the liquid 5, the refractive index of the insulating film 1a at its top-layer interface does not differ too significantly, compared with use of a dry-system objective lens. A sufficient suppression effect against thin-film interference can thus be obtained. Therefore, the liquid immersion technology using a liquid 5 whose refractive index is greater than that of air (i.e., using a liquid 5 having a refractive index greater than 1) is within the scope of the present invention.

While defect inspection effects based on liquid immersion have heretofore been described, the following three factors need to be considered when a liquid 5 is selected:

(1) In terms of resolution improvement, a liquid higher in refractive index (e.g., an oil-based liquid having a refractive index of about 1.6) is preferable.

(2) In terms of thin-film interference suppression, a liquid having a refractive index equivalent to that of the insulating film 1a (e.g., the pure water, alcohol-containing liquid, or mixture of both that ranges from about 1.3 to about 1.5 in refractive index) is preferable.

(3) Since the wafer 1 is to be immersed, a liquid less influential on device characteristics (e.g., pure water, an alcohol-containing liquid, or a mixture of both) is preferable.

(The above does not apply to destructive inspection.)

Pure water, an alcohol-containing liquid (such as isopropyl alcohol), a fluorine-containing liquid, or even an oil-containing liquid or a mixture of these liquids is likely to be usable as the liquid for liquid-immersion inspection. In consideration of factors (1), (2), and (3) listed above, however, pure water, alcohol-containing liquid, or a mixture of both is preferable. To allow for the ease of supply inside a clean room, it is ideal to use a liquid mixture obtained by adding a trace amount of alcohol-containing liquid to pure water.

Also, the illumination light used for the liquid-immersion inspection is effective anywhere in the range from a visible region to a deep ultraviolet region. The usable types of light sources include a mercury lamp, a Xenon lamp, and other discharge tubes, or a laser light source. In addition, the illumination light can have a single wavelength width or a broad-band wavelength (multi-spectrum included).

Figure 4:
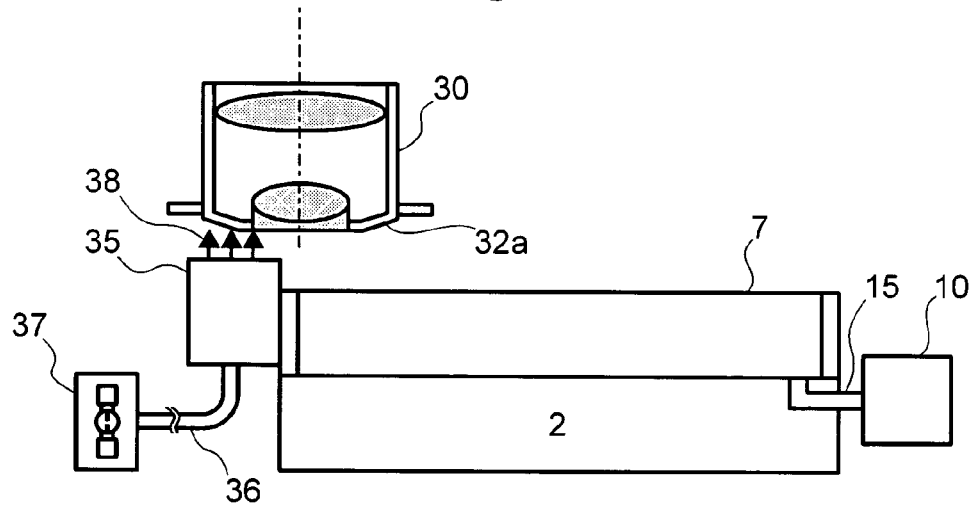
FIG. 4 is a configuration diagram for realizing a method of retaining a surface-treated state of the front end of an objective lens according to the present invention.
Figure 5:
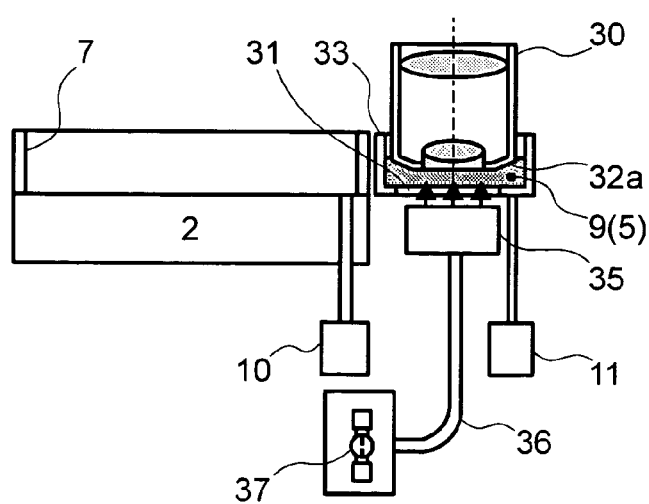
FIG. 5 is a configuration diagram for realizing a method of retaining a cleaned and surface-treated state of the front end of an objective lens according to the present invention.

Next, examples of preventing air bubbles from sticking to a lens surface, and thus smoothing the flow of a liquid in order to suppress entrainment of the bubbles and other unfavorable events, are described below using FIGS. 3 to 5.

Figure 3:
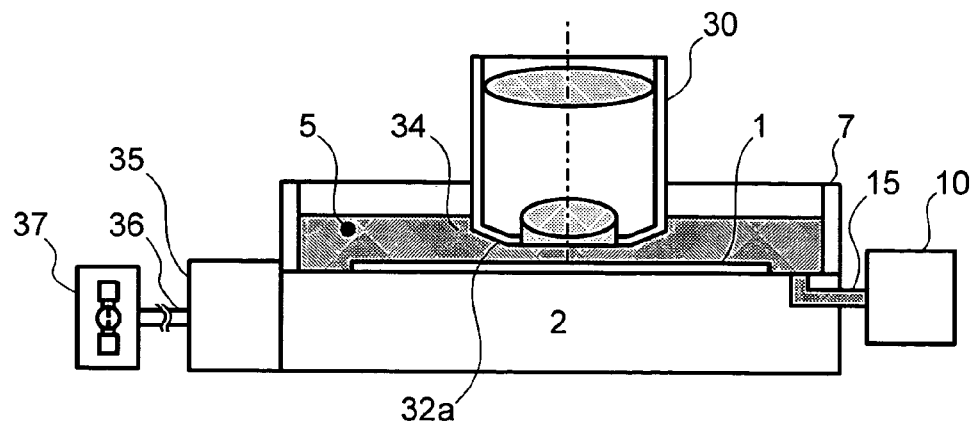
FIG. 3 is an explanatory diagram of total liquid immersion according to the present invention.

A diagram of a liquid-immersion section is shown in FIG. 3. A front surface 32a of an objective lens 30 and a wafer 1 are immersed in a liquid 5 supplied to a liquid tank 7. A pipe 15 is connected between the liquid tank 7 and a liquid supplying and discharging unit 10. Before the wafer 1 is loaded into a chuck 2, the liquid tank 7 is empty. After the wafer 1 has been loaded into the chuck 2, the liquid 5 is supplied to the liquid tank 7. The objective lens 30 and the wafer 1 are thus filled with the liquid. After the above loading, an image of a positioning mark on the wafer 1 is acquired using an image sensor 44 or the like. After this, an image processor unit 54 detects a position of the mark, then the wafer 1 is aligned by positioning stages via a mechanical controller 58, and inspection is started. To inspect the wafer 1 over its entire surface, the wafer requires scanning in a horizontal direction. When the wafer is scanned, waves are likely to occur on the surface of the liquid 5, thus causing bubbles to enter between the objective lens 30 and the wafer 1. If such a bubble is formed as an optical image, defect incorrect-detection results since the presence itself of the bubble is not a defect. In order to prevent such incorrect-detection, a flow-straightening plate 34 is disposed at the front-end portion of the objective lens 30. If a lens-barrel of the objective lens 30 is about 40 mm in outside diameter, an outside diameter of the flow-straightening plate 34 is about 60 to 80 mm. The flow-straightening plate 34 produces a smooth flow of the liquid 5 between the wafer 1 and the objective lens 30, and suppresses the occurrence of events such as entrainment of the bubbles.

Also, it may be advisable to surface-modify the front-end portion 32a of the objective lens 30 in terms of structure. The surface modification is intended to prevent air bubbles from sticking to the lens surface and to make smoothly the flow of the liquid 5. For these purposes, the lens surface and a lens holder of the lens front surface 32a are surface-modified beforehand. For example, the front-end portion 32a of the lens is pre-coated with a titanium-oxide film to provide hydrophilic treatment. Since the hydrophilic treatment varies characteristics with time, an ultraviolet (UV) light source 37 is disposed at a peripheral portion of the liquid tank 7 and the UV light emitted from the light source is introduced into a UV-light irradiating portion through an optical-fiber cable 36. When the wafer 1 is being unloaded from the chuck 2, UV light 38 is irradiated onto the front surface 32a of the objective lens, as shown in FIG. 4, in order to produce a photocatalytic effect for retained hydrophilic property.

If dirt etc. adheres to the front-end portion 32a of the objective lens 30, quality of the optical image will be fallen. A method of cleaning for removing the dirt is described below using FIG. 5. While the wafer 1 is being unloaded, the front-end portion 32a of the objective lens 30 is immersed in an objective-lens cleaning tank 33 to which is supplied a liquid 9 (5) having a cleaning effect. At the same time, the front-end portion 32a of the objective lens 30 can also be improved in hydrophilic property by irradiating UV light from the UV-light irradiating portion 35 onto the front-end portion 32a of the objective lens 30 through a transparent window 31. An alcohol-containing liquid, pure water, a fluorine-containing liquid, or the like may be usable as the cleaning liquid 9. Also, if the same liquid as the liquid 5 used for liquid immersion in inspection is used as the cleaning liquid 9, a liquid supplying and discharging unit 11 and piping can be shared and this is advantageous in terms of apparatus space-saving and cost reduction. The cleaning liquid 9 (5) to and from the cleaning tank 33 is supplied and discharged by the liquid supplying and discharging unit 11.

Figure 6:
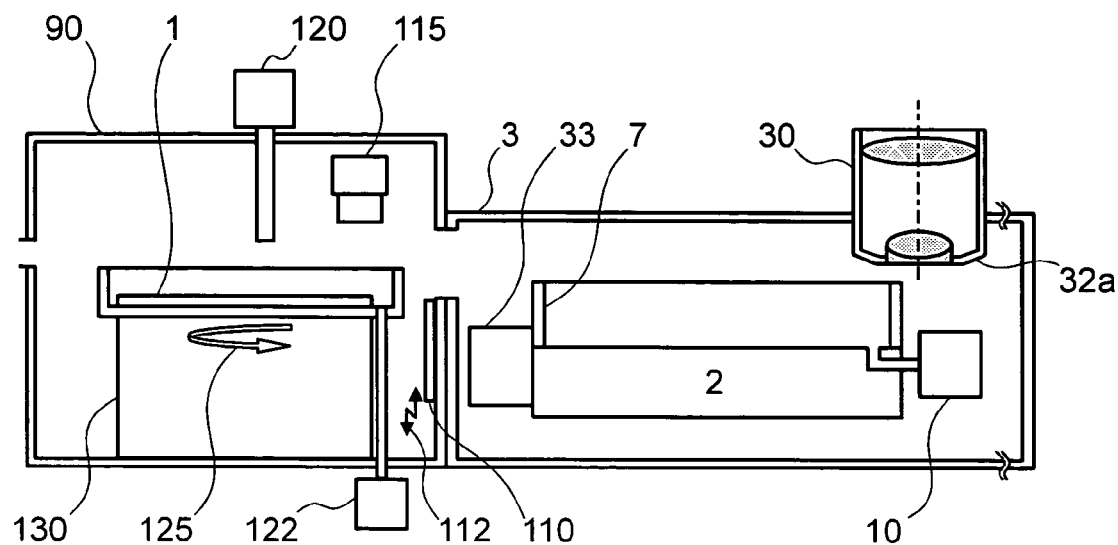
FIG. 6 is a configuration diagram showing an inspection preparation chamber for conducting a wafer pre-inspection preparation process, and an inspection station that uses total liquid immersion, in the present invention.
Figure 31:
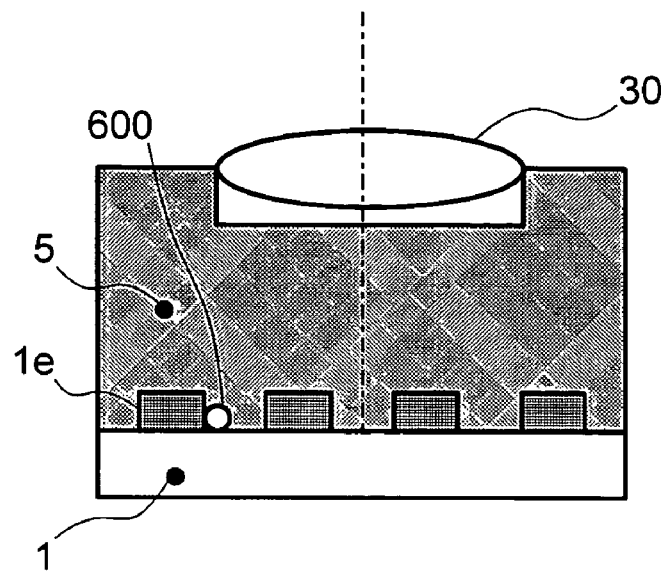
FIG. 31 is a diagram showing an example in which a pattern formed on the wafer to be inspected is immersed in a liquid according to the present invention.

Next, an example of a preparatory process for liquid-immersion inspection is described below using FIG. 6. By the way, as shown in FIG. 31, defect inspection using the liquid immersion scheme poses problems associated with pattern materials and structure. FIG. 31 shows an example in which a pattern 1e formed on a wafer 1 to be inspected is immersed in a liquid 5. When the surface of the wafer 1 is immersed in the liquid 5 in order to inspect the wafer 1, a stepped portion of the pattern 1e is unlikely to be filled with the liquid and thus an air bubble 600 may stick. If the air bubble 600 actually sticks, an image thereof will be formed in an optical image obtained from enlarged projection through an objective lens 30. However, since the image of the air bubble 600 does not signify a shape defect in the pattern 1e, this image should not be detected as a defect in the pattern 1e. A process step for removing the air bubble 600 is therefore required in the preparatory process for liquid-immersion inspection.

Figure 32:
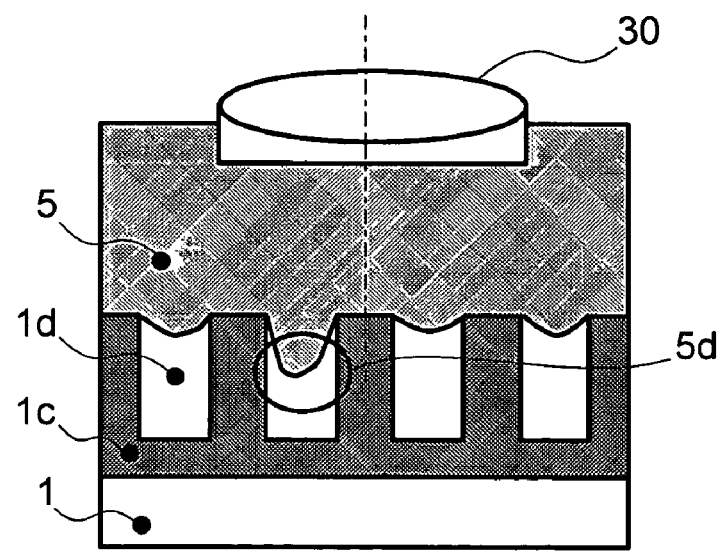
FIG. 32 is a diagram showing an example in which, when a contact hole (through-hole) existing before a conductive material is embedded therein is to be inspected, when the surface of the contact hole is immersed in a liquid 5.

Also, as shown in FIG. 32, contact holes (through-holes) without a conductive material embedded therein are to be inspected very often during defect inspection. A contact holes 1d is hollow when it does not have an embedded conductive material. When the surface of the contact holes 1d is immersed in the liquid 5, if this contact holes has less than a specific diameter, the liquid 5 does not enter in the contact holes. When an inspection is to be conducted in a liquid-immersed condition, therefore, if the contact holes 1d is formed with a uniform shape and diameter, it is desirable that the liquid 5 also be of a similar shape at a surface layer of the contact hole. However, if, during the liquid-immersion inspection, the liquid 5 has taken a different shape such as a shape 5d, the contact hole portion at 5d will be detected as an uneven optical image, and thus, a spurious defect is likely to be detected. This is why an interfacial shape of the liquid 5 at the surface layer of the contact holes 1d also needs to be formed into a similar shape during a preparatory process for the liquid-immersion inspection.

For this reason, as a preparatory process for the liquid-immersion inspection, the wafer 1, after being transferred to an inspection preparation chamber 90, is mounted on a notch-detecting rotation unit 130, then the rotation unit 130 is rotated in a direction of an arrow 125, and a notch is detected using a notch detector 115. After this, the notch is pre-positioned in a required direction and the wafer 1 is loaded into an inspection station 3, mounted in a chuck 2, and immersed in the liquid 5 to undergo actual inspection.

Process steps for removing the air bubble 600 and for forming also the interfacial shape of the liquid 5 at the surface layer of the contact hole 1d into a similar shape are required in such a preparatory process for the liquid-immersion inspection.

Figure 7:
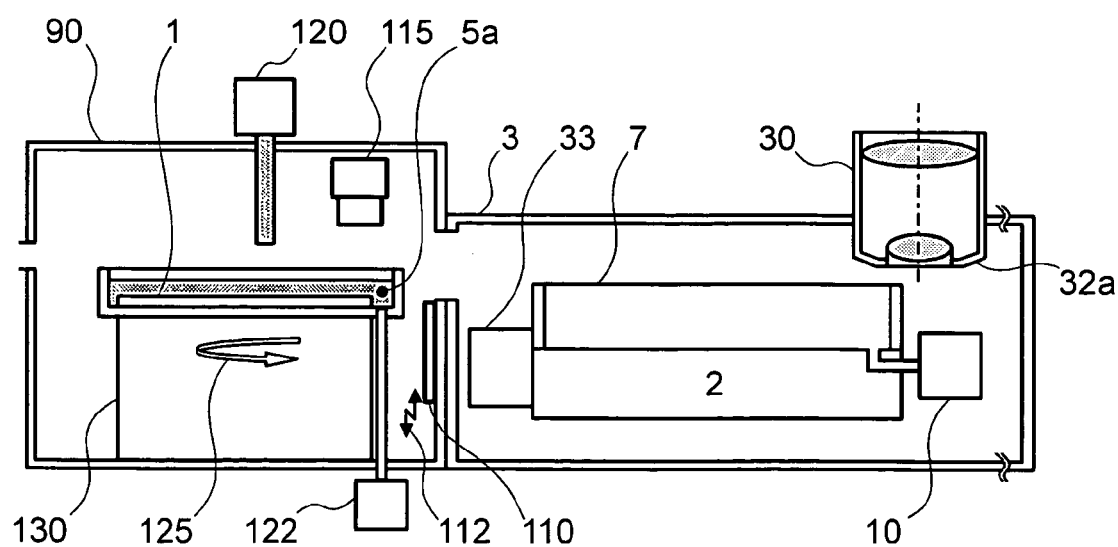
FIG. 7 is an explanatory diagram of a combination of an inspection preparation chamber for conducting a wafer pre-inspection preparation process, and an inspection station that uses total liquid immersion, in the present invention.

A schematic configuration of an optical-type visual inspection apparatus having an inspection station 3 and inspection preparation chamber 90 based on total liquid immersion is shown in FIG. 7.

As shown in FIG. 7, a notch in a wafer 1 is pre-positioned in a required direction in the inspection preparation chamber 90 and then the wafer 1 has its surface immersed in a liquid 5a supplied from a pre-inspection liquid immersion unit 120. Mere immersion could result in air bubbles left sticking to the surface of the wafer 1. For this reason, the rotation unit 130 rotates the wafer 1 beforehand (this is referred to as wafer in-liquid spinning). This removes any sticking air bubbles, and when a contact hole 1d is already formed, creates a uniform interfacial shape of the liquid 5a at a surface layer of the contact hole 1d. Desirably, the liquid 5a supplied from the pre-inspection liquid immersion unit 120 is spread over the entire surface of the wafer 1, so the liquid 5a needs only to have an excellent hydrophilic property and does not need to be the same as a liquid 5 used for the inspection (or both liquids can be of the same characteristics). If the liquid 5a and the inspection liquid 5 differ in characteristics and the occurrence of respective vapors is likely to cause a chemical reaction, an opening/closing unit 112 for opening and closing both the preparation chamber 90 and the inspection station 3 by means of a partition 110 can be provided to prevent the chemical reaction from occurring.

Figure 8:
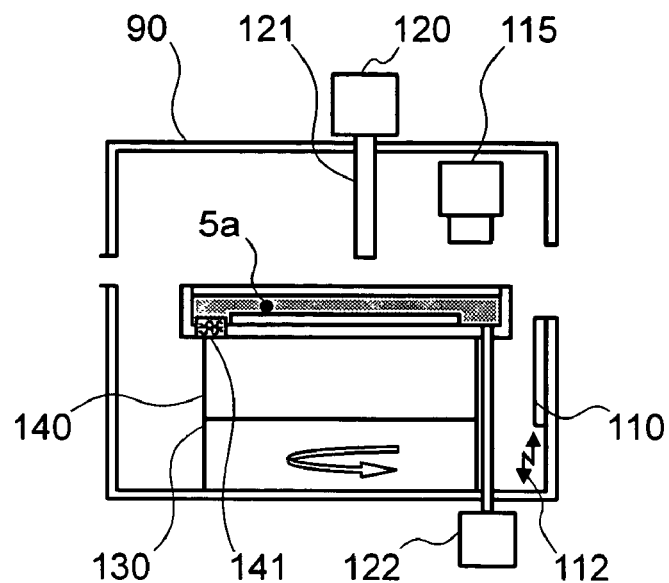
FIG. 8 is an explanatory diagram of a wafer pre-inspection liquid-immersion preparation process according to the present invention.

Another processing method for removing air bubbles is shown in FIG. 8. A notch in a wafer 1 is positioned in a required direction and then the wafer 1 has its surface immersed in a liquid 5a supplied from a pre-inspection liquid immersion unit 120. Next, the liquid is vibrated using an ultrasound vibration source 141 driven by a vibration generator 140 (this is referred to as wafer in-liquid ultrasound vibration). This removes sticking air bubbles from the wafer 1, and when a contact hole 1d is already formed, creates a uniform interfacial shape of the liquid 5 (5a) at a surface layer of the contact hole 1d as shown in FIG. 32.

Briefly, as shown in FIG. 26, pre-alignment by V-notch matching (step S263), pre-inspection liquid immersion (step S264), wafer interfacial bubble removal (step S265), and pre-inspection liquid removal (step S266, but no liquid removal from the wafer surface) are conducted in a pre-inspection preparatory process. Wafer interfacial bubble removal is implemented using a wafer in-liquid spinning method, a wafer in-liquid ultrasound vibration method, or a depressurizing process, as described above. Even when using a depressurizing process to reduce a pressure of the inspection preparation chamber, it is possible to remove the air bubbles sticking to the wafer 1 (wafer interfacial bubble removal).

Next, an embodiment for drying a wafer on which a liquid-immersion inspection was performed is described below using FIG. 9. An inspected wafer 1 is carried into an inspection preparation chamber 90, then the moisture sticking to the wafer 1 is dried, and the wafer 1 is returned to a cassette 80 (steps S274, S275). Spin-drying by a rotation unit 130 is executed as a moisture-drying function for the wafer 1 in the preparation chamber 90. At this time, since the moisture flies about, it could re-stick to the wafer 1, but this time, in the form of mist, after the wafer has been dried. In order to prevent re-sticking, a gas is supplied using a blower 131 and the gas is vented via a suction unit 132, whereby mist can be discharged smoothly from the inspection preparation chamber 90 and can thus be prevented from re-sticking to the wafer 1. A drying method using an air knife is shown in FIG. 10. After the inspected wafer 1 has been transferred to the inspection preparation chamber 90, a gas is sprayed onto the surface of the wafer 1 by a gas-spraying device 150 to blow away the liquid on the surface of the wafer 1. The liquid particles thus blown away are taken into a suction unit 155, whereby the liquid particles that have been blown away in a mist-like form can also be discharged from the inspection preparation chamber 90 and re-sticking to the wafer 1 can be prevented.

Figure 9:
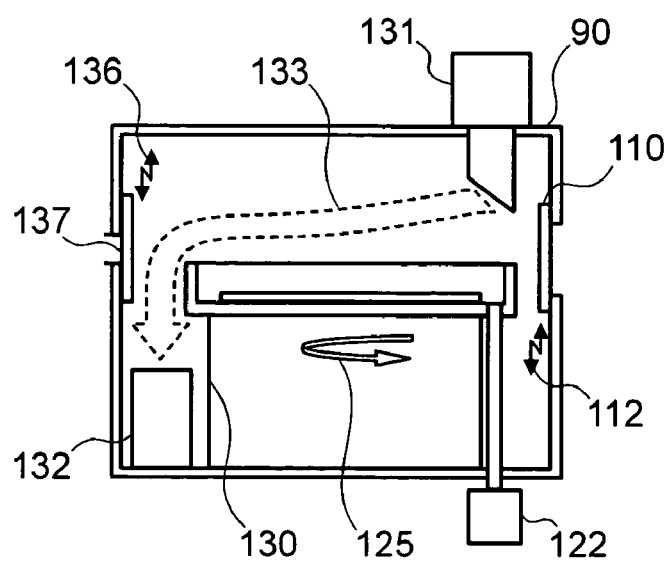
FIG. 9 is an explanatory diagram of a first example of a wafer post-inspection drying process according to the present invention.
Figure 10:
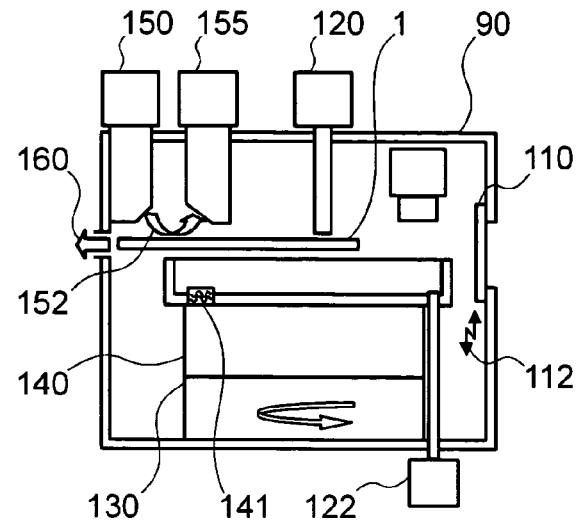
FIG. 10 is an explanatory diagram of a second example of a wafer post-inspection drying process according to the present invention.

Air, a nitrogen gas, vapors of isopropyl alcohol, or the like may be usable as the gas blown and sprayed in FIGS. 9 and 10. When vapors of isopropyl alcohol are used, in particular, a higher drying effect is expected to be obtainable.

In addition, reduced-pressure IPA (isopropyl alcohol) vaporizing is possible as a method of wafer drying.

Next, embodiments/examples of inspection based on local liquid immersion are described below using FIGS. 11 to 20.

Figure 11:
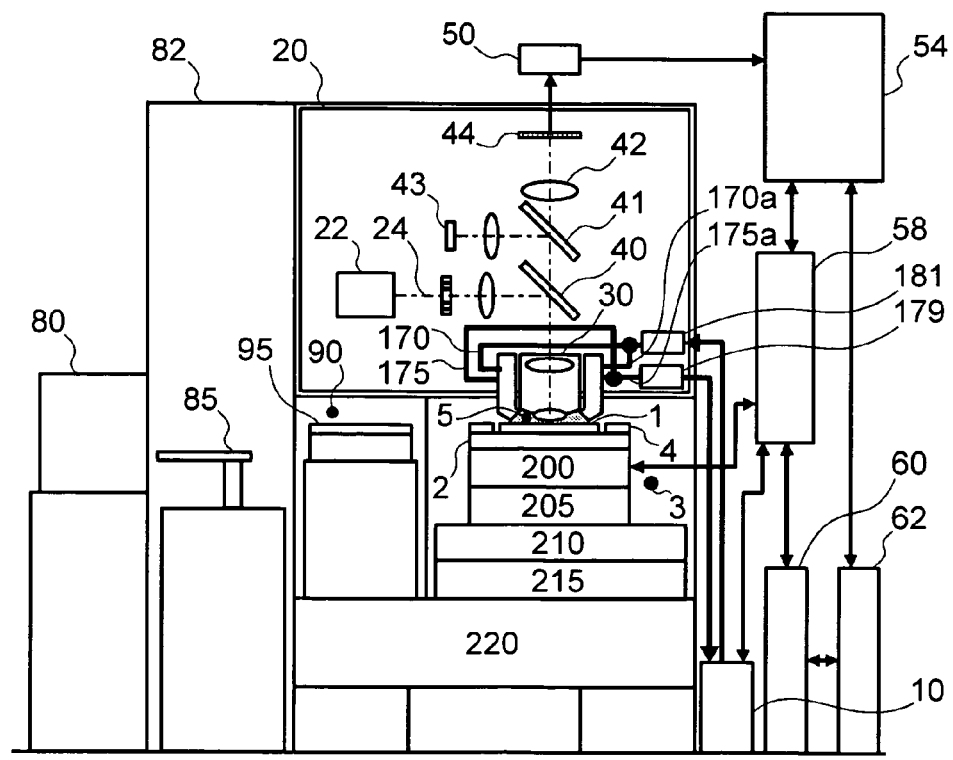
FIG. 11 is a configuration diagram showing an embodiment of an optical-type visual inspection apparatus that uses local liquid immersion according to the present invention.

The technique for total liquid immersion of a wafer 1, shown in FIG. 1, and a local liquid immersion technique for immersing in a liquid only a clearance present between an objective lens 30 and the wafer 1 are usable as liquid immersion techniques. The local liquid immersion technique is shown in FIG. 11. Basic configuration is much the same as that of FIG. 1, except for an interior of the inspection station 3 shown in FIG. 1. For example, for a linear type of image sensor 44, images are acquired while the wafer 1 is being moved at a fixed speed. A liquid 5 is fed from a liquid supplying and discharging unit 10 into a liquid supply controller 181 at a specific pressure (flow rate). The liquid, after having its flow rate, temperature, and other factors controlled by the liquid supply controller 181, is supplied to the surface of the wafer 1 through a pipe 170 disposed in front of a position at which the wafer 1 moves past the objective lens 30. The liquid that has been supplied to the wafer 1 flows under the objective lens 30, in a direction where the wafer 1 moves (here, on the figure, from left to right). After flowing past the objective lens 30, the liquid 5 is discharged by being introduced into a liquid discharge controller 179 through a pipe 175a. The liquid thus discharged into the liquid discharge controller 179 flows out into the liquid supplying and discharging unit 10, whereby, even when the wafer 1 is moving, the clearance between the objective lens 30 and the wafer 1 can be filled with the liquid at all times. When the moving direction of the wafer 1 becomes opposite (here, on the figure, from right to left), the liquid is supplied to the surface of the wafer 1 through a pipe 170a, flows under the objective lens, and is forcibly taken into the pipe 175. When an image is to be acquired during movement of the wafer 1, therefore, the liquid is supplied to a supply position before the view field of the objective lens 30 passes on the wafer (sample) 1 and the liquid is discharged from a discharge position after the view field of the objective lens 30 passed on the wafer 1. The liquid supply controller 181 and the liquid discharge controller 179 are piped at respective specific pressures to the liquid supplying and discharging unit 10. The supplying and discharging scheme for this liquid is described below using FIG. 12. The flow of the liquid 5 from the liquid supply controller 181 is branched into two pipes, 170 and 170a. For example, when the wafer 1 is moving at a fixed speed in a direction of an arrow 211, a valve 171 on the pipe 170 is open and a valve 171a on the pipe 170a is in a closed condition. Hence, supply of the liquid to the wafer 1 uses only the pipe 170. After being supplied to the surface of the wafer 1 through the pipe 170, the liquid 5 flows between the objective lens 30 and the wafer 1 and is then guided to the liquid discharge controller 179 through the pipe 175a having an open valve 176a. At this time, a valve 176 on the pipe 175 is in a closed condition. When the wafer 1 is moving in an opposite direction to that of the arrow 211, the valve 171a at a supply side is open and the valve 171 is closed, whereas the valve 176 at a discharge side is open and the valve 176a is closed. By conducting such opening/closing control of the valves, the clearance between the objective lens 30 and the wafer 1 can be filled with the liquid at all times, even when the moving direction of the wafer 1 is reversed. The liquid supply controller 181 includes a regulator 182 for adjusting a supply rate of the liquid, an oxygen concentration regulator 183 for the liquid, and a liquid temperature controller 184. The liquid discharge controller 179 has a mounted regulator 177 for adjusting a discharge rate of the liquid. It is desirable that the oxygen concentration regulator 183 (also having a bubble-removing function based on pressure reduction) should further be capable of (1) preventing oxidation of the wafer 1 due to the presence of the liquid 5, and (2) removing any micro-bubbles contained in the liquid supplied. The types of oxygen concentration regulator 183 useable for the liquid include a device that utilizes Henry's law. Also, the liquid 5 changes in refractive index with a change in temperature. Since the objective lens 30 is optically designed with the refractive index of the liquid as a specific value, aberration of the lens increases as its refractive index changes. The temperature controller 184 is therefore required for suppression of changes in the refractive index of the objective lens. The usable types of temperature controller 184 include a device that utilizes the Peltier effect (thermoelectric cooling). Desirably, the oxygen concentration regulator 183 and the temperature controller 184 are provided, even in the wafer total liquid immersion scheme shown in FIG. 1.

In particular, during wafer edge inspection based on local liquid immersion, since there occurs the level difference for thickness of the wafer, the liquid 5 flows out from the wafer edge onto the surface of the chuck 2. For this reason, the clearance between the objective lens 30 and the wafer 1 cannot be filled with the liquid 5. A stepped portion 4 equivalent to the thickness of the wafer 1, therefore, needs to be provided in proximity to an outer surface of the wafer 1. Thus, even when the outer surface of the wafer 1 is to be inspected, the clearance between the objective lens 30 and the wafer 1 can be filled with the liquid 5 since a slight clearance is only left between the outer surface of the wafer 1 and the stepped portion 4 (see FIG. 11). In addition, the clearance between the objective lens 30 and the wafer 1 can be filled with the liquid 5 by filling the clearance between the outer surface of the wafer 1 and the stepped portion 4, with the liquid 5, during a time interval from completion of wafer loading to the start of inspection.

Figure 13:
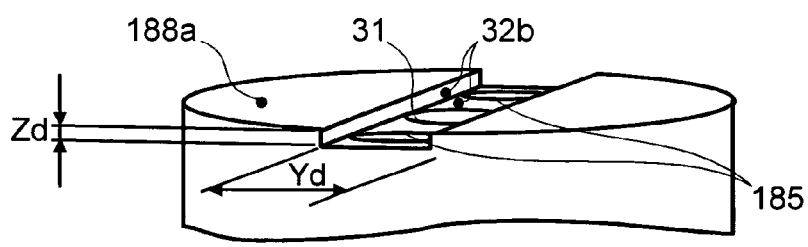
FIG. 13 is a perspective view showing an example of a front-end shape of the objective lens shown in FIG. 12 for a local liquid immersion method.

An external view of the front-end portion of the objective lens 30 that faces the wafer 1 is shown in FIG. 13. Glass 31 is a window that transmits illumination light and the light reflected/diffracted by a pattern. Liquid supply and discharge ports 185 are arranged symmetrically with the window 31 as their center. A groove formed with width Yd and depth Zd is a region to be filled with the liquid supplied. Of all plane portions of the objective lens 30, plane portion 188a is the plane portion brought closest to the wafer 1, and a spacing between the plane portion 188a and the wafer 1 acts as a working distance (WD). It is desirable that the amount of liquid left on the wafer 1 should be minimized. It is necessary, therefore, for the liquid to be reduced in the amount of overflow reaching a portion other than the groove (e.g., in a direction within a horizontal face, orthogonal to a traveling direction of the wafer 1). A reduction effect against the amount of liquid left on the wafer 1 is expected to be obtainable by conducting hydrophilic surface treatment of a groove portion 32b that is to be filled with the liquid, and hydrophobic surface treatment of the plane portion 188a other than the groove. A similar reduction effect is likewise anticipated by adjusting WD. A desirable WD value is up to about 0.7 mm (further desirably, up to about 0.3 mm). A relational expression relating to the amount of liquid supplied and the amount of its discharge, is shown as equation (4) below. When dimension Z for filling the region with the liquid is taken as Zd+WD, dimension Y for filling the region with the liquid, as Yd, a stage-scanning velocity as Vst, a liquid supply rate as Vin, and a liquid discharge rate as Vout, liquid supply rate Vin should be greater than liquid discharge rate Vout. This relational expression is shown as equation (4).

$$Vin \geq Vout = (Zd+WD) \times Yd \times Vst \quad (4)$$

Figure 14A:
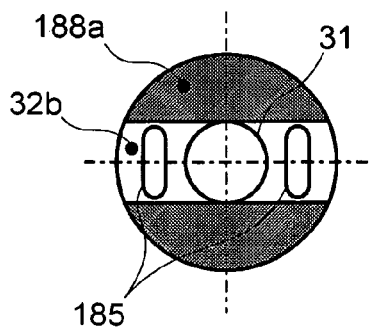
FIGS. 14A and 14B are plan views each showing an example of a front-end shape of the objective lens shown in FIG. 12 for a local liquid immersion method.
Figure 14B:
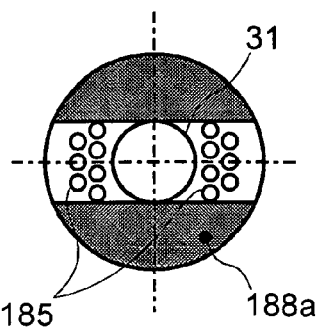

Examples of shapes of the liquid supply and discharge ports 185 are shown in FIGS. 14A and 14B. In FIG. 14A, two liquid supply and discharge ports 185, one at each side of the window 31, are formed symmetrically with the window 31 as their center. In FIG. 14B, a plurality of holes is provided to form a liquid supply and discharge port 185 at each side.

Thus, the supply and discharge rates of the liquid can be made relatively equal between central and peripheral portions of the groove.

Figure 15:
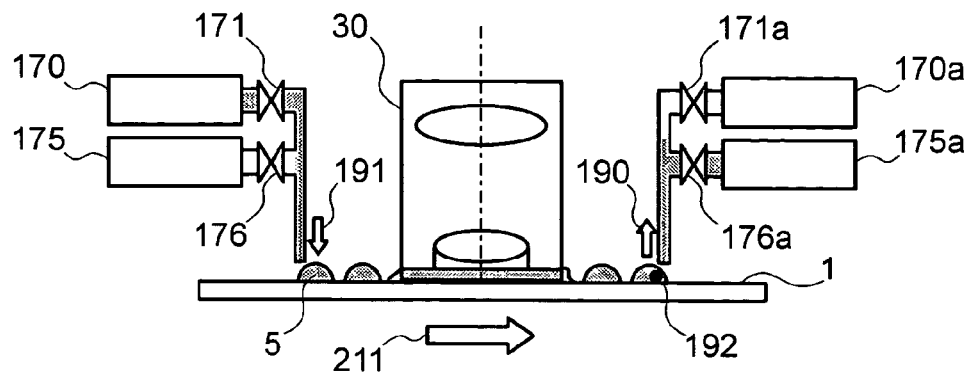
FIG. 15 is an explanatory diagram of a liquid supplying and discharging structure separated from the lens-barrel of an objective lens for a local liquid immersion method according to the present invention.
Figure 16:
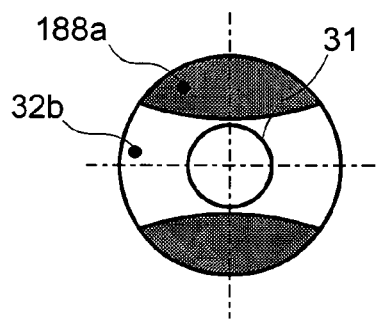
FIG. 16 is a plan view showing an example of a front-end shape of the objective lens shown in FIG. 15 for a local liquid immersion method.

An embodiment for realizing local liquid immersion by using liquid supply and discharge ports separated from a lens-barrel of an objective lens 30 is shown in FIG. 15. When a wafer 1 is to be scanned in a direction of an arrow 211, a valve 171 of a liquid supply controller 170 is opened and a liquid 5 is continuously supplied from a position 191 separate from the lens-barrel, to the wafer 1. The supplied liquid 5, because of its surface tension, sticks to the surface of the wafer 1 and as the wafer 1 moves, a grooved region of the objective lens 30 is filled with the liquid 5. After the liquid 5 has subsequently flown past the objective lens 30, a valve 176*a* of a liquid discharge controller 175*a* is opened to take in the liquid 5 from a position 190 separate from the lens-barrel, thus discharging the liquid. When the scanning direction of the wafer 1 is reversed, valves 171, 171*a*, 176, and 176*a* arranged respectively at the liquid supply controller 170, 170*a* and liquid discharge controller 175, 175*a* are each opened/closed as in FIG. 12. A shape of the front-end portion of the objective lens 30 that faces the wafer 1 is shown in FIG. 16. Of all sections of the objective lens 30, plane 188*a* is the plane brought closest to the wafer 1, and plane portion 32*b* is a grooved section to be filled with the liquid. Near a window 31, the groove is reduced in width to be easily filled with the liquid and hence to prevent an air layer from being easily formed.

Figure 12:
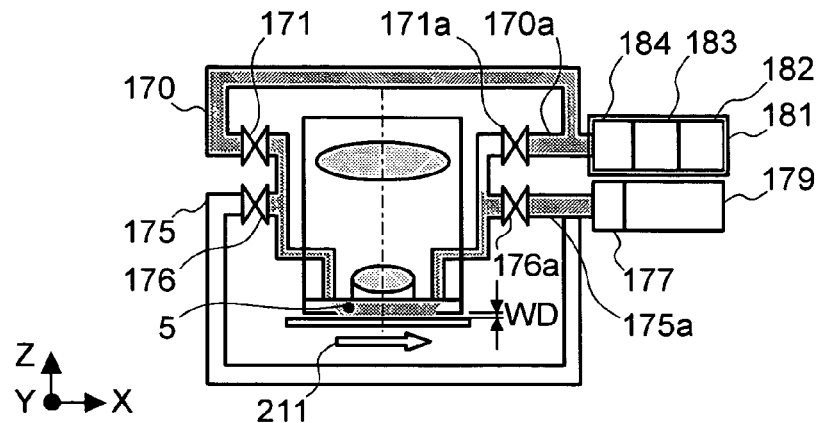
FIG. 12 is an explanatory diagram of a first embodiment of a liquid supplying and discharging structure built into the lens-barrel of an objective lens for a local liquid immersion method according to the present invention.
Figure 17:
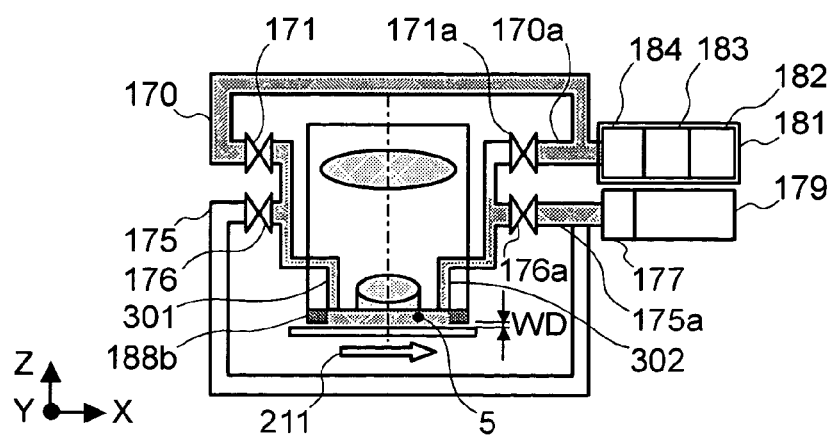
FIG. 17 is an explanatory diagram of a second embodiment of a liquid supplying and discharging structure built into the lens-barrel of an objective lens for a local liquid immersion method according to the present invention.
Figure 18:
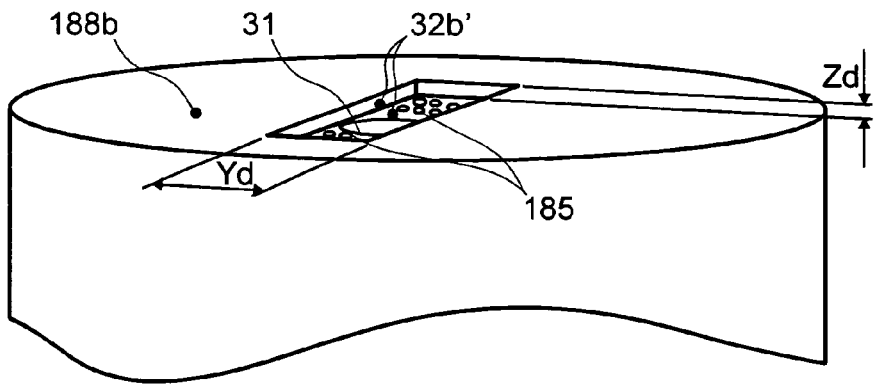
FIG. 18 is a perspective view showing an example of a front-end shape of the objective lens shown in FIG. 17 for a local liquid immersion method.
Figures 19A, 19B, 19C:
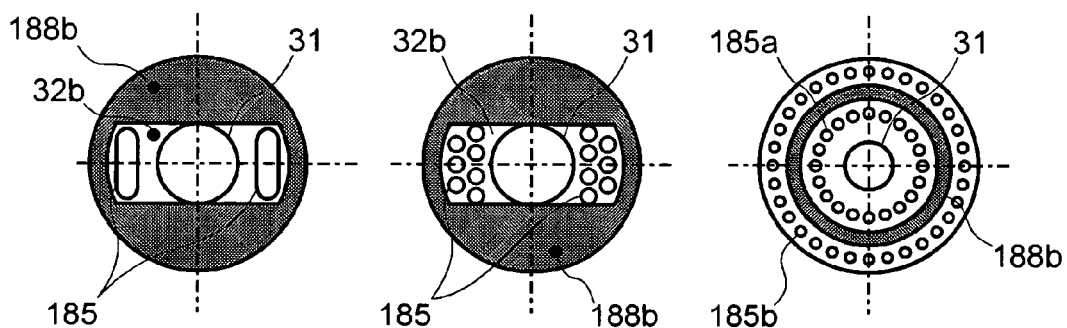
FIGS. 19A, 19B, and 19C are plan views each showing an example of a front-end shape of the objective lens shown in FIG. 17 for a local liquid immersion method.

Next, a modified example of the local liquid immersion scheme shown in FIG. 12 is described below using FIG. 17. The operations of liquid supply controller 181 and liquid discharge controller 179, and opening/closing states of each of valves 171, 171*a*, 176, and 176*a* are the same as those of FIG. 12. A groove 32*b'* to be filled with a liquid 5 is formed with a wall plane portion 188*b* on the entire periphery of the groove. A shape of the front-end portion of an objective lens 30 that faces a wafer 1 is shown in FIG. 18. At the groove 32*b*, a stepped plane portion 188*b* is also provided in a traveling direction of a stage. Examples of a shape of this groove are shown in FIGS. 19A, 19B, and 19C. In FIG. 19A, two liquid supply and discharge ports 185, one at each side of a window 31, are formed symmetrically with the window 31 as their center. In FIG. 19B, a set of holes is provided to form a liquid supply and discharge port 185 at each side. In FIG. 19C, the stepped plane portion 188*b* brought closest to the wafer 1 is constructed into a ring form to allow response to two-dimensional movements of the wafer. Inside this ring is formed a liquid supply port 185*a* to supply the liquid 5. Supply of the liquid from an inside-diametric portion of the ring causes an overflow from the stepped plane 188*b*. The overflow is discharged from a plurality of discharge ports 185*b* arranged outside the stepped plane portion 188*b*. Thus, the groove is shaped so that even if the wafer 1 moves in various directions on the plane, the stepped plane portion 188*b* can be filled with the liquid from inside and discharged from outside. This shape is also effective for observing detected defects, because, when a moving distance between defects is to be minimized for defect observation. The wafer needs to be moved in various directions according to a particular position of a defect.

Figure 20:
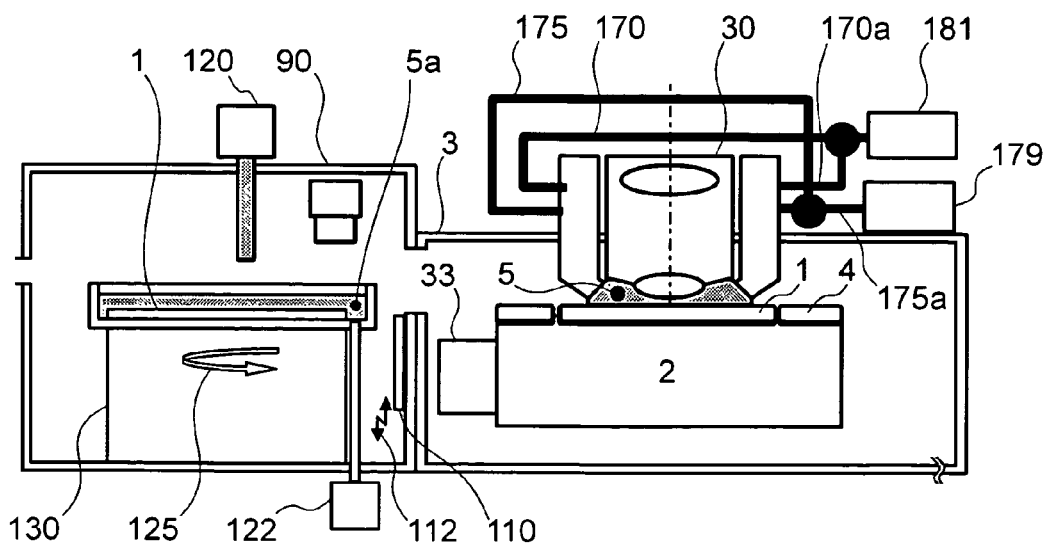
FIG. 20 is an explanatory diagram of a combination of an inspection preparation chamber for conducting a wafer pre-inspection preparation process, and an inspection station that uses local liquid immersion, in the present invention.

Even for inspection based on the local liquid immersion heretofore described, it is desirable that as described in the embodiment of inspection based on total liquid immersion, a pre-inspection preparatory process for the wafer and a post-inspection drying process for the wafer should be performed. A schematic configuration of an optical-type visual inspection apparatus having an inspection station 3 and an inspection preparation chamber 90 based on local liquid immersion is shown in FIG. 20.

Figure 21:
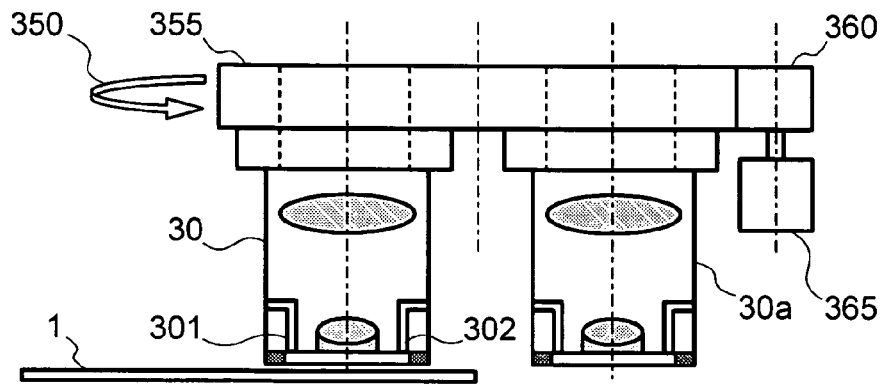
FIG. 21 is a diagram showing an example in which multiple objective lenses different in imaging magnification are mounted in a liquid immersion system according to the present invention.
Figure 22:
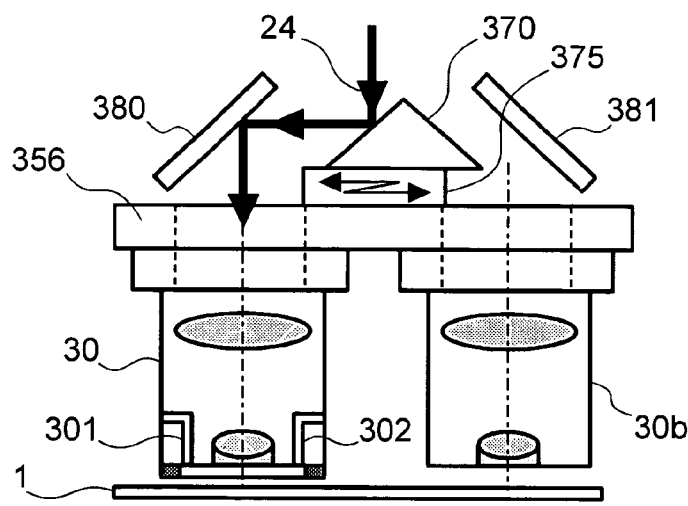
FIG. 22 is a diagram showing an example in which multiple objective lenses are mounted in both a liquid immersion system and a dry system according to the present invention.
Figure 23A:
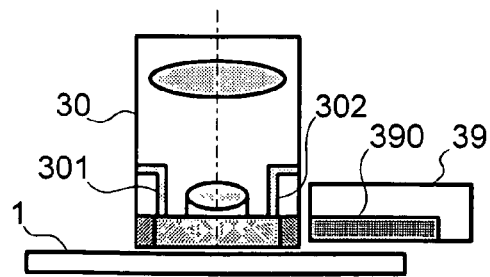
FIGS. 23A and 23B are diagrams each showing an example in which a single independent objective lens is switched between a liquid immersion system and a dry system according to the present invention.
Figure 23B:
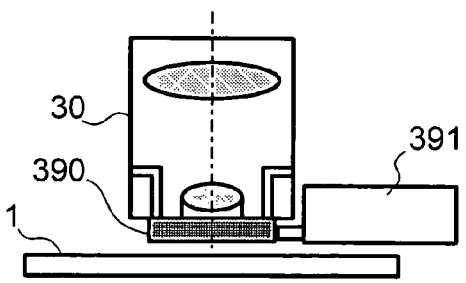

Next, an example of changing a magnification of an objective lens in the optical-type visual inspection apparatus is described below using FIG. 21. The inspection apparatus usually makes it necessary to change the magnification of the objective lens. For example, high-magnification inspection is efficient for the wafer that requires high-sensitivity inspection, and low-magnification high-throughput inspection is efficient for the wafers that do not pose a problem even when they are inspected with relatively low sensitivity. Therefore, an inspection magnification usually needs to be changed according to the inspection sensitivity required. To change the magnification significantly, it is valid to replace the objective lens. A method of mounting multiple objective lenses is shown in FIG. 21. Multiple objective lenses 30 and 30*a* are arranged at a revolver 355. At least one of these objective lenses is a liquid-immersion objective lens. The revolver 355 is rotated horizontally in a direction of an arrow 350 by rotation of a gear 360 connected to a motor 365. The objective lens 30 being used is thus replaced. However, if liquid supply and discharge ports are disposed at a front-end portion of the objective lens 30, liquid piping between a liquid supplying and discharging unit and the objective lens needs to be temporarily disconnected when the revolver 355 is rotated, and the piping is to be reconnected after the revolver has stopped rotating. Therefore, a structurally simple configuration with the objective lens 30 and the liquid supply and discharge ports constructed in a separate form, as shown in FIG. 15, is effective for revolver usage. Also, a liquid-immersion system objective lens and a dry-system objective lens may need to be mounted with mixed state. An embodiment for realizing such mixed mounting is shown in FIG. 22. When a liquid-immersion system objective lens 30 and a dry-system objective lens 30*b* are to be mounted, both lenses are fixed to a base 356. For inspection with the liquid-immersion system objective lens 30, illumination light 24 is reflected toward a mirror 380 via a triangular mirror 370 and guided to the liquid-immersion system objective lens 30. For inspection with the dry-system objective lens 30*b*, a triangular mirror sliding unit 375 is moved to reflect the illumination light toward a mirror 381 via the triangular mirror 370. Thus, it becomes possible to guide the illumination light to the dry-system objective lens 30*b* and form an optical image using the dry-system objective lens 30*b*. As a result, an optical system (illumination optical system and detection optical system) other than an optical path ranging from the triangular mirror 370 to the objective lenses 30 and 30*b* serves as a common optical path, hence allowing the liquid immersion system and the dry system to be switched with a relatively simple configuration. Configurations in which the liquid-immersion system objective lens 30 can also be used for the dry system are shown in FIGS. 23A and 23B. FIG. 23A shows an objective lens 30 aberration-corrected for liquid immersion use. For inspection based on liquid immersion, a clearance between the objective lens 30 and a wafer 1 is filled with a liquid. When the liquid-immersion objective lens 30 is to be used for a dry system, the clearance present between the objective lens 30 and the wafer 1 is filled with a gas such as air. In this case, since a refractive index differs between a liquid and air, aberration increases and this extremely deteriorates optical images in resolution. Flat-parallel-plate glass 390 for conducting corrections for the deterioration, and a flat-parallel-plate glass sliding unit 391 are therefore equipped. As shown in FIG. 23B, when the liquid-immersion objective lens 30 is to be used in a dry condition, the flat-parallel-plate glass sliding unit 391 moves the flat-parallel-plate glass 390 to dispose it between the objective lens 30 and the wafer 1. Thus, even when the liquid-immersion objective lens 30 is used in a dry condition, aberration can be corrected for, whereby the liquid-immersion objective lens 30 can be used in two different ways. The flat-parallel-plate glass 390 is disposed with a gap so as not to come into contact with the wafer 1.

Figure 24:
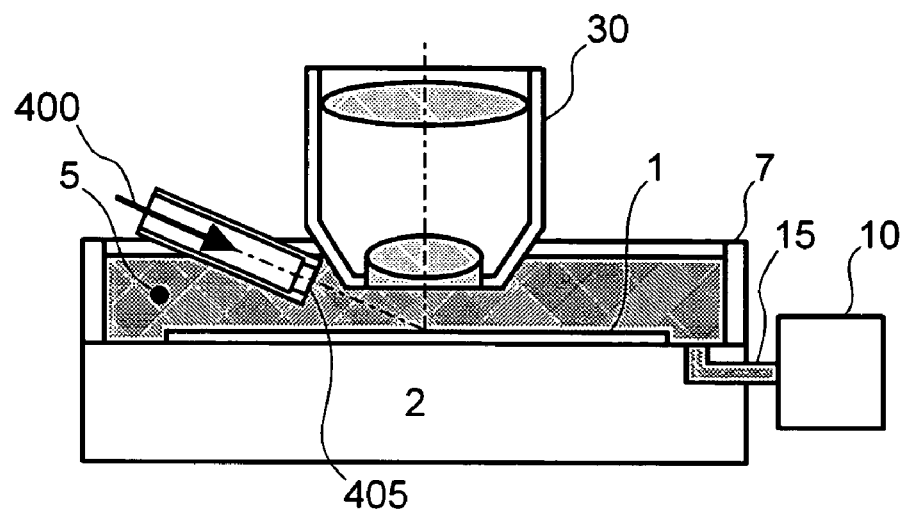
FIG. 24 is a diagram showing an example of a dark-field detection scheme that uses total liquid immersion according to the present invention.

Next, examples of dark-field detection schemes based on liquid immersion are described below using FIGS. 24 and 25. FIG. 24 is a diagram showing an example of a dark-field detection scheme which uses total liquid immersion. In this dark-field detection scheme, a wafer 1 is illuminated with oblique illumination (off-axis illumination) 400, then the light scattered/diffracted by an extraneous substance or pattern present on the wafer 1 is captured using an objective lens 30, and a dark-field image is thus formed. To suppress changes in an incident angle due to the occurrence of waves on the surface of a liquid 5, illumination light needs to be irradiated through an optical window 405 immersed in the liquid 5. The configuration from the objective lens 30 to an image sensor 44 is the same as the configuration shown in FIG. 1. Also, it becomes possible, by disposing a spatial filter at a position of an exit pupil of the objective lens 30 or at a position conjugate to the exit pupil, and cutting off a specific frequency band, to shield diffraction pattern obtained from a periodic pattern. This method makes it possible to detect only the light scattered from foreign particles, and is therefore advantageous for inspection of foreign particles and surface irregularity defects. Although FIG. 24 shows one oblique illumination system only, illumination from multiple directions is possible by mounting multiple oblique illumination systems.

Figure 25:
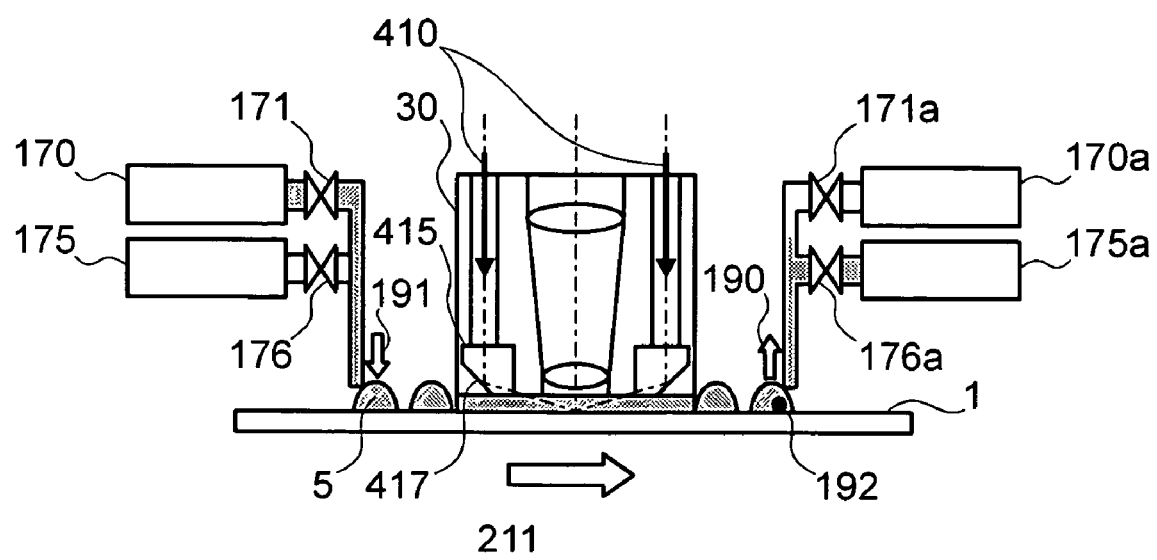
FIG. 25 is a diagram showing an example of a dark-field detection scheme that uses local liquid immersion according to the present invention.

FIG. 25 is a diagram showing an example of a dark-field detection scheme which uses local liquid immersion. As shown in FIG. 25, an oblique illumination optical path 410 is provided outside an objective lens 30 and dark-field illumination light is made to enter a prism 415. The illumination light is irradiated so as to direct obliquely by reflecting a surface 417 of the prism 415 to a view field of the objective lens 30 on the wafer 1. The light reflected/diffracted from a foreign particle or pattern present on a wafer 1 is captured using an objective lens 30, and a dark-field image is thus formed. Although FIG. 25 shows two oblique illumination systems, 410 and 415, with the objective lens 30 interposed between them, further adding dark-field illumination systems is also easily conceivable. In an extreme case, all directional dark-field illumination with an optical axis of the objective lens 30 as its center is possible by using a ring-form prism.

Configurations of dark-field illumination schemes based on liquid immersion have been described above, and these schemes, compared with dark-field illumination schemes with a dry system, are advantageous in terms of (1) resolution improvement and (2) stabilization of scattered-light detection intensity by suppression of thin-film interference. Thus, high-sensitivity inspection is possible, even in dark-field illumination schemes.

In addition, mixed configurations of the dark-field illumination schemes shown in FIGS. 24 and 25, and the bright-field illumination schemes shown in FIGS. 1 and 11, is also possible. In these mixed configurations, bright-field and dark-field composite illumination, bright-field independent illumination, and dark-field independent illumination are possible and ability of defect detection for a variety of defects can be strengthened.

An example of inspection process flow in the embodiments heretofore described is shown in FIG. 26. First, wafers waiting for the start of inspection are stored in a cassette 80. One such wafer is transferred to an inspection preparation chamber 90 by a transfer system 85 (step S262). The wafer 1 thus transferred has its V-notch (or orientation flat) detected, and the wafer is pre-aligned in its θ direction (step S263). Next, pre-inspection liquid immersion is conducted (step S264) and bubbles at an interface between the wafer and the liquid are removed (step S265). The bubbles can be removed by (1) wafer in-liquid spinning or (2) wafer in-liquid ultrasound vibration or using (3) a depressurizing process or the like. Removal of the bubbles is followed by removal of the pre-inspection liquid (step S266). At this time, since a drying process is not conducted, the liquid that may have entered micro-stepped pattern portions of the wafer remains sticking to these micro-stepped portions. Next, the wafer is loaded into an inspection station 3 (step S267). The wafer disposed in a chuck of the inspection station is immersed in an inspection liquid (step S269). As described above, (1) wafer total liquid immersion, (2) partial liquid immersion, or the like can be used as a method of the above liquid immersion. In step S268, the liquid supplied for the immersion is provided with temperature adjustment (by, for example, thermoelectric cooling using the Peltier effect), bubble removal (by, for example, depressurization), oxygen concentration control (by, for example, processing under a low oxygen concentration atmosphere), and/or the like. These forms of liquid immersions are followed by wafer scanning and image detection. After these, defect inspection based on image comparisons by means of an image processor unit 54 is conducted (step S270). After the inspection, the liquid for the pre-inspection liquid immersion is removed (step S271) and then the wafer is unloaded from the inspection preparation chamber 90 (step S272). The wafer thus unloaded is then dried (step S274). Either (1) reduced-pressure IPA (isopropyl alcohol) vaporizing, (2) wafer spinning, (3) jet spraying of a gas, or the like is usable as the drying process. The wafer, after being dried, is returned to the cassette by the transfer system (step S275). This completes the inspection sequence. When an inspection is not being conducted, in order for an objective lens area immersed in the liquid to be activated (step S273), UV light may be irradiated onto the plane of the objective lens that faces the wafer. Although a simplified inspection sequence has been described above, changing the inspection sequence and/or omitting unnecessary process steps can consider easily and is within the scope of the present invention.

Next, examples of a forming process for semiconductor wafer patterns are described below using FIGS. 27A, 27B, and 27C. A forming process for semiconductor wafer patterns is shown in FIG. 27A. First, a pattern material is deposited on a wafer 1 and a resist is applied. Next, patterns are exposed, developed, and etched. After this, the resist is removed and then the wafer is cleaned and undergoes defect inspection. The above deposition is repeated if these patterns are laminated with further patterns. Process flow relating to cleaning and defect inspection, is shown in FIG. 27B. In the cleaning step, pure-water cleaning follows chemical cleaning. Chemical cleaning and pure-water cleaning may be repeated multiple times according to the type of object cleaned. After this, drying is provided and then the sequence proceeds to a defect inspection step. In this step, a defect inspection using an optical-type visual inspection apparatus is performed with the wafer immersed in a liquid. After this, the wafer is dried, at which time, drying is repeated twice between cleaning and the defect inspection. A shortcut process for reducing the drying operations to one time is shown in FIG. 27C. For example, cleaning and the defect inspection are conducted with one set of apparatus. In this case, liquid immersion is conducted after chemical cleaning and pure-water cleaning, and drying is executed after the defect inspection. The drying step in this case is only performed once after the inspection, and this method is valid for simplifying the manufacturing process. An embodiment pertaining to such a simplified process is shown in FIG. 28. A wafer that underwent resist removal and was returned to a cassette 80 is carried into a cleaning chamber 325 by a transfer system 85. In the cleaning chamber, there are multiple liquid tanks 330a, 330b, and 330c (each including a water-washing bath), in which the wafer is cleaned and washed in water. A cleaning liquid is supplied from a tank 335a. After the final water-washing, the wafer is loaded into an inspection station having optical system disposed therein, and is pre-aligned in a θ direction via a notch detector. Next, the water is mounted in a wafer chuck 2 and a defect inspection based on liquid immersion is conducted. After the inspection, the wafer is carried into the cleaning chamber, in which the water is then washed in water as required. This wafer is further carried into a drying compartment 300 in order to be subjected to, for example, depressurizing/superheat IPA vaporizing. The inside of the drying chamber 305 is adjusted to a required temperature by a heating plate 320, vapors of IPA 315 are fed into the chamber 305, and pressure is reduced by a vacuum pump 310. Thus, the moisture sticking to the water patterns can be dried. After being dried, the wafer is returned to the cassette 80.

Figure 29:
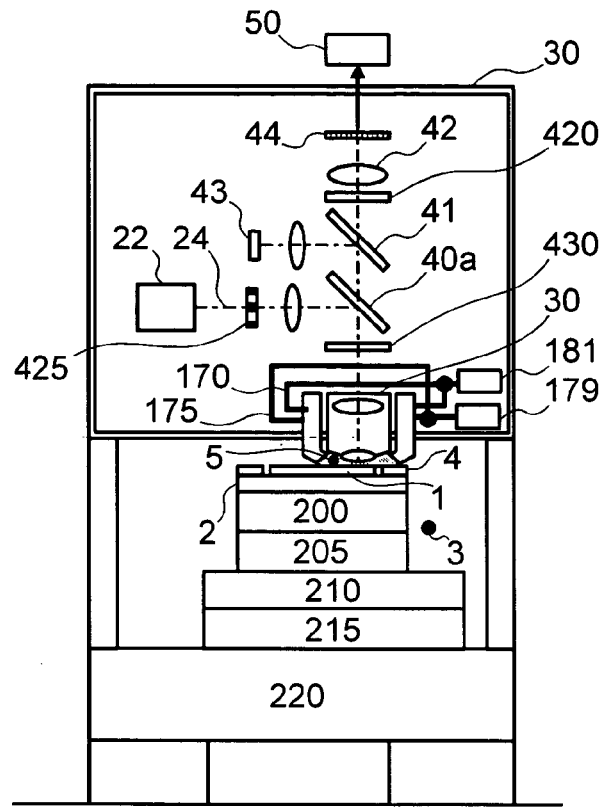
FIG. 29 is an explanatory diagram of the optical system utilizing the liquid immersion technology according to the present invention.

Next, an example of configuration of the visual inspection optical system which utilizes liquid immersion is described below using FIG. 29. Also, a procedure for improving the optical system in resolution is shown below.

(1) A space between an objective lens 30 and a wafer 1 is immersed in a liquid, and resolution is improved.

(2) In the incident illumination/bright-field detection scheme, when Koheler illumination is applied, an image of a light source 22 is formed on an aperture stop 425. This image is further formed on a pupil of the objective lens 30. If the aperture stop 425 has a ring-form aperture portion, the light illuminating one point on the wafer 1 becomes oblique illumination light not having a vertical illumination light component. Use of the illumination light improves high-frequency MTF (Modulation Transfer function) of a spatial frequency.

(3) Furthermore, when a polarizing type of beam splitter 40a is used, the light reflected from the beam splitter 40a changes into linearly polarized light. On passing through a wavelength plate 430, the linearly polarized light further changes into elliptically polarized-light to provide the wafer 1 with incident illumination. After the illumination, the polarized light has its polarized state modulated when the light is reflected, diffracted, and/or scattered from a pattern on the wafer 1. These light beams pass through the wavelength plate 430 once again and enter the polarizing-type beam splitter 40a. The polarized light that has passed through the polarizing-type beam splitter 40a forms an optical image of the wafer 1, and an image sensor 44 detects the image. In this way, the polarizing-type beam splitter 40a functions as a light analyzer. Therefore, the polarized state of the illumination light is pre-adjusted according to the polarized state existing when the light is reflected, diffracted, and/or scattered from a pattern on the wafer 1. Thus, the optical image formed of the regular reflected light, high-order diffracted light, and scattered light passing through the polarizing-type beam splitter 40a, is adjusted to become an image advantageous for defect detection. The image advantageous for defect detection refers to an image whose defective portions can be improved in contrast.

(4) When the wafer 1 is illuminated using the ring-form aperture stop 425 described in item (2) above, 0th-order light (regular reflected light) and high-order diffracted light are separated at the pupil of the objective lens 30. For this reason, the patterns on the wafer 1 can be detected in an enhanced condition by disposing, at a position of the pupil, a spatial filter 420 for adjusting transmissivity and relative phase contrast for both the 0th-order light and high-order diffracted light (first-order or higher). The above is based on the principles of phase contrast microscopy. The pupil of the objective lens 30 is usually formed therein, and therefore, there is no space available to dispose the spatial filter. Hence, a position conjugate to the pupil of the objective lens 30 is provided and the spatial filter 420 is provided at this conjugate position. This makes it possible to improve optical images in resolution and to form images advantageous for defect detection.

A liquid immersion method was described in item (1) above, and resolution improvement technology, in items (2) to (4) above. Combining these techniques allows further improvement of optical system in resolution and provides a greater advantage in high-sensitivity inspection.

Figure 30:
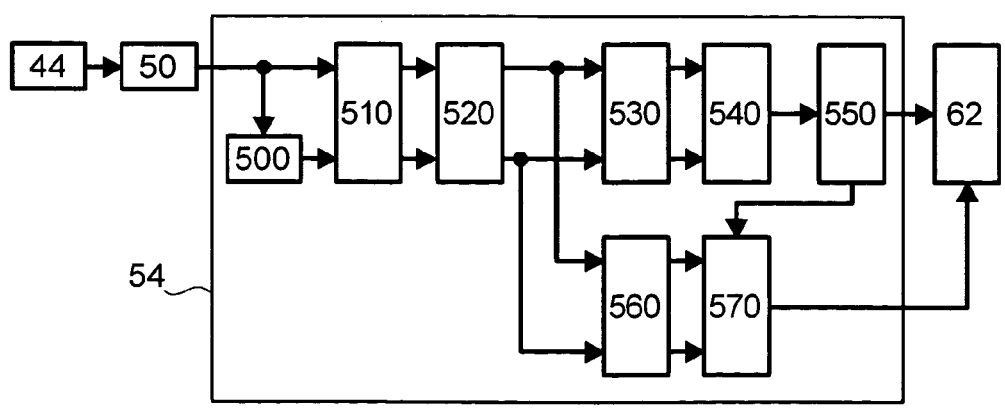
FIG. 30 is a functional configuration diagram of the image processor unit in an optical-type visual inspection apparatus that uses liquid immersion according to the present invention.

Next, a more specific embodiment of the image processor unit 54 shown in FIGS. 1 and 11 is described below using FIG. 30. The image of a wafer 1 that has been detected by an image sensor 44 (in the present embodiment, a linear image sensor) is input as a digital image to an image processor unit 54 via an A/D converter 50. The input image is branched into a position deviation detector 510 and a delay memory 500. The delay memory 500 sends to the position deviation detector 510 an image delayed by a time associated with adjacent dies (in the case of die comparison) or a time delayed by a time associated with adjacent cells (in the case of cell comparison). The image sent to the position deviation detector 510 is an image of an adjacent die (or cell) having the same design pattern formed on the wafer 1. The amount of deviation in position between the above two images is detected by the position deviation detector 510 and then the deviation is adjusted for accurate position matching at an image alignment unit 520. Position matching at the image alignment unit 520 is conducted in sub-pixel units. A differential image is acquired from the position-matched images by a differential-image arithmetic unit 530. Based on characteristic values of the differential image, a judgment is conducted on a defect candidate 550 by a defect judgment unit 54. The characteristic values serving as the base for defect judgment by the defect judgment unit 540 include a gray scale difference, a size (including a area and a projection length) exceeding a gray scale difference threshold, brightness of the detected image, contrast of the image, and defect coordinate information. After being detected by the defect judgment unit 540, the defect candidate 550 has its defect coordinate information input to a defect classification unit 570. The images of an adjacent die that were branched from the image alignment unit 520 are temporarily stored in an image memory 560, and an image associated with the coordinates of the defect candidate that have been input to the defect classification unit 570 can be read out from the image memory 560. The defect classification unit 570 classifies defects or defect candidate by using the image of an adjacent die that has been read out. The information of classification results and the defect candidate 550 are stored into a data server 62. The presence/absence of foreign particles and pattern defects, fatal influence with respect to device characteristics, and the like are judged at the defect classification unit 570. Therefore, the coordinate information and size of and classification results on the defect candidate 550 are stored as information into the data server 62, from which various information of defect is then further sent for a defect observation step.

While defect inspection methods based on liquid immersion, liquid-immersion inspection sequences, and the like have been described above, combination of respective embodiments/examples, use of composite illumination, modification and omission of an inspection sequence, and the like are easily devisable and their contents are embraced in the present invention.

The invention may be embodied in other specific forms without departing from the spirit or essential characteristics thereof. The present embodiment is therefore to be considered in all respects as illustrative and no restrictive, the scope of the invention being indicated by the appended claims, rather than by the foregoing description, and all changes which come within the meaning and range of equivalency of the claims are therefore intended to be embraced therein.

What is claimed is:

1. A method of inspecting defects, said method comprising the steps of:
    immersing a sample to be inspected in a liquid at a pre-inspection liquid immersion unit and conducting interfacial bubble removal of the sample;
    transferring the sample from the pre-inspection liquid immersion unit onto a table of a detection optical system;
    forming, in a state where a clearance between a sample and a front-end portion of detection optical system is filled with a liquid, an optical image of the sample by use of the detection optical system;
    acquiring as an image signal by use of an image sensor, the optical image formed in said step of forming the optical image of the sample; and
    detecting defects on the sample on the basis of the image signal acquired in said acquisition step.

2. The method of inspecting defects according to claim 1, wherein, in said step of forming the optical image, during the state where the clearance between the sample and the front-end portion of the detection optical system is filled with the liquid, the liquid is continuously supplied to the clearance between the sample and the front-end portion and the supplied liquid is continuously discharged at a rate lower than a supply rate of the liquid.

3. The method of inspecting defects according to claim 1, wherein, in said step of forming the optical image, the state where the clearance between the sample and the front-end portion is filled with the liquid is formed in a local region on the sample, between the sample and the front-end portion.

4. The method of inspecting defects according to claim 3, wherein the state where the local region between the sample and the front-end portion of the detection optical system is filled with the liquid is realized by supplying the liquid to a supply position before a view field of the detection optical system passes on the sample and discharging the liquid from a discharge position after the view field of the detection optical system passed on the sample.

5. The method of inspecting defects according to claim 1, wherein, in said step of forming the optical image, during the state where the clearance between the sample and the front-end portion of the detection optical system is filled with the liquid, an entire surface of the sample is covered with the liquid.

6. The method of inspecting defects according to claim 1, wherein, in said step of forming the optical image, the state where the local region between the sample and the front-end portion of the detection optical system is filled with the liquid is realized by placing the sample in a tank filled with the liquid and immersing the front-end portion of the detection optical system in the liquid of the tank.

7. The method of inspecting defects according to claim 1, wherein, in said step of forming the optical image, illumination of the sample is one of an incident illumination scheme, an off-axis illumination scheme and a mixed scheme of an incident illumination scheme and an off-axis illumination scheme.

8. The method of inspecting defects according to claim 1, wherein, in said step of forming the optical image, light is illuminated via the detection optical system to the sample and light reflected from the sample is used to obtain focus detection information which indicates a positional relationship between a focus of the detection optical system and the sample.

9. The method of inspecting defects according to claim 1, said method further comprising the step of drying the sample that has gone through said step of detecting defects.

10. The method of inspecting defects according to claim 1, wherein in the step of immersing the sample, said interfacial bubble removal of the sample is conducted by at least one of rotating the sample in the liquid, vibrating the liquid by using an supersonic wave vibration or decompression inside the pre-inspection liquid immersion unit.

11. The method of inspecting defects according to claim 1, said method further comprising the step of prior to said step of forming the optical image, conducting a surface activation treatment for an area in which the detection optical system is to be immersed in the liquid.

12. A method of inspecting defects, said method comprising the steps of:
    immersing a sample to be inspected in a liquid at a pre-inspection liquid immersion unit and conducting interfacial bubble removal of the sample;
    transferring the sample from the pre-inspection liquid immersion unit onto a table of a detection optical system;
    forming, in a state where a clearance between a sample and a front-end portion of detection optical system is filled with a liquid, an optical image of the sample by illuminating the sample by use of elliptically polarized light and detecting reflected/diffracted light generated from the sample by the illumination, in a polarized form with the detection optical system;
    acquiring as an image signal by use of an image sensor, the optical image formed in said step of forming the optical image of the sample; and
    detecting defects on the sample on the basis of the image signal acquired in said acquisition step.

13. The method of inspecting defects according to claim 12, wherein, in said step of forming the optical image, during the state where the clearance between the sample and the front-end portion of the detection optical system is filled with the liquid, the liquid is continuously supplied to the clearance between the sample and the front-end portion and the supplied liquid is continuously discharged at a rate lower than a supply rate of the liquid.

14. The method of inspecting defects according to claim 12, wherein, in said step of forming the optical image, the state where the clearance between the sample and the front-end portion is filled with the liquid is formed in a local region on the sample, between the sample and the front-end portion.

15. The method of inspecting defects according to claim 14, wherein the state where the local region between the sample and the front-end portion is filled with the liquid is realized by supplying the liquid to a supply position before a view field of the detection optical system passes on the sample and discharging the liquid from a discharge position after the view field of the detection optical system passed on the sample.

16. The method of inspecting defects according to claim 12, wherein, in said step of forming the optical image, during the state where the clearance between the sample and the front-end portion of the detection optical system is filled with the liquid, an entire surface of the sample is covered with the liquid.

17. The method of inspecting defects according to claim 12, wherein, in said step of forming the optical image, the state where the clearance between the sample and the front-end portion of the detection optical system is filled with the liquid, is realized by placing the sample in a tank filled with the liquid and immersing the front-end portion of the detection optical system in the liquid of the tank.

18. The method of inspecting defects according to claim 12, wherein, in said step of forming the optical image, illumination of the sample is one of an incident illumination scheme, an off-axis illumination scheme and a mixed scheme of an incident illumination scheme and an off-axis illumination scheme.

19. The method of inspecting defects according to claim 12, wherein, in said step of forming the optical image, light is illuminated via the detection optical system to the sample and light reflected from the sample is used to obtain focus detection information which indicates a positional relationship between a focus of the detection optical system and the sample.

20. The method of inspecting defects according to claim 12, said method further comprising the step of drying the sample that has gone through said step of detecting defects.

21. The method of inspecting defects according to claim 12, wherein in the step of immersing the sample, said interfacial bubble removal of the sample is conducted by at least one of rotating the sample in the liquid, vibrating the liquid by using an supersonic wave vibration or decompression inside the pre-inspection liquid immersion unit.

22. The method of inspecting defects according to claim 12, said method further comprising the step of, prior to said step of forming the optical image, conducting a surface activation treatment for an area in which the detection optical system is to be immersed in the liquid.

23. An apparatus for inspecting defects, said apparatus comprising:
  pre-inspection liquid immersion unit for immersing a sample to be inspected and conducting interfacial bubble removal of the sample;
  a table unit which mounts a sample, said table unit being movable in a plane;
  a transferrin unit for transferrin the sample from the re-inspection liquid immersion unit to the table unit;
  a detection optical system which has an objective lens for forming an optical image of the sample mounted on said table unit;
  a liquid immersion unit which fills a clearance between the sample and a front-end portion of said detection optical system, with a liquid;
  an image sensor which acquires the optical image of the sample formed by said detection optical system in a state where the clearance between the sample and the front-end portion of said detection optical system is filled with the liquid, said image sensor further transmitting the optical image in an image signal form; and
  an image processor unit which processes the image signal transmitted from said image sensor, and detects defects on the sample.

24. The apparatus for inspecting defects according to claim 23, wherein said liquid immersion unit includes a liquid supply unit for continuously supplying the liquid so that the clearance between the sample and the front-end portion of said detection optical system is filled with the liquid, and a liquid discharge unit for continuously discharging the liquid supplied from said liquid supply unit.

25. The apparatus for inspecting defects according to claim 23, wherein said liquid immersion unit includes a liquid supply unit for supplying the liquid so that the clearance between the sample and the front-end portion of said detection optical system is locally filled with the liquid, and a liquid discharge unit for discharging the liquid supplied locally from said liquid supply unit.

26. The apparatus for inspecting defects according to claim 23, wherein said liquid immersion unit includes a liquid immersion tank for immersing the sample in the liquid and placing the sample in a totally liquid-immersed state.

27. The apparatus for inspecting defects according to claim 23, wherein said liquid immersion unit fills the clearance between the sample and the front-end portion of said detection optical system means, with pure water or an alcohol-containing liquid or a fluorine-containing liquid or a liquid mixture of any two or more of these liquids.

28. The apparatus for inspecting defects according to claim 23, said apparatus further comprising an off-axis illumination system for illuminating light to the sample without using the objective lens of said detection optical system.

29. The apparatus for inspecting defects according to claim 23, said apparatus further comprising a dry unit which dries the sample.

30. The apparatus for inspecting defects according to claim 23, wherein, in the state where the clearance between the sample and the front-end portion of said detection optical system is filled with the liquid by said liquid immersion unit, the objective lens of said detection optical system forms an optical image of the sample with a numerical aperture (NA) value greater than 1.0.

* * * * *

UNITED STATES PATENT AND TRADEMARK OFFICE
CERTIFICATE OF CORRECTION

PATENT NO. : 7,599,545 B2  Page 1 of 1
APPLICATION NO. : 10/893988
DATED : October 6, 2009
INVENTOR(S) : Shibata et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1387 days.

Signed and Sealed this

Twenty-eighth Day of September, 2010

David J. Kappos
*Director of the United States Patent and Trademark Office*